US006605456B1

United States Patent
Bird et al.

(10) Patent No.: US 6,605,456 B1
(45) Date of Patent: Aug. 12, 2003

(54) NUCLEIC ACIDS ENCODING IKR-2, A PROTEIN KINASE RELATED TO THE I KAPPA B KINASES

(75) Inventors: Timothy A. Bird, Bainbridge Island, WA (US); G. Duke Virca, Bellevue, WA (US)

(73) Assignee: Immunex Corporation, Seattle, WA (US)

( * ) Notice: Subject to any disclaimer, the term of this patent is extended or adjusted under 35 U.S.C. 154(b) by 0 days.

(21) Appl. No.: 09/509,800

(22) PCT Filed: Aug. 4, 1999

(86) PCT No.: PCT/US99/17578

§ 371 (c)(1),
(2), (4) Date: Jun. 9, 2000

(87) PCT Pub. No.: WO00/08179

PCT Pub. Date: Feb. 17, 2000

Related U.S. Application Data

(60) Provisional application No. 60/118,783, filed on Feb. 5, 1999, provisional application No. 60/099,973, filed on Sep. 11, 1998, and provisional application No. 60/095,269, filed on Aug. 4, 1998.

(51) Int. Cl.[7] .............................. C12N 9/12; C12N 1/20; C12N 15/00; C12N 5/00; C07H 21/04
(52) U.S. Cl. ................ 435/194; 435/252.3; 435/320.1; 435/325; 435/410; 536/23.2
(58) Field of Search .............................. 435/194, 252.3, 435/320.1, 325, 410, 254.1, 6; 536/23.2

(56) References Cited

U.S. PATENT DOCUMENTS 5,776,717 A   7/1998  Cao
5,837,514 A * 11/1998 Cao ........................... 435/194

FOREIGN PATENT DOCUMENTS

WO   WO 99/58558 A2   11/1999
WO   WO 00/73469 A2   12/2000

OTHER PUBLICATIONS

Regnier et al. Identification and characterization of an IKB kinase. Cell, vol. 90, pp. 373–383, 1997.*
Marra et al. EST database Accession #AA218405, 1997.*
Marra et al. EST database Accession #AA265250, 1997.*
Bandman et al., GeneSeq Database Accession No. AAY44240; Feb. 28, 2000.

(List continued on next page.)

*Primary Examiner*—Ponnathapu Achutamurthy
*Assistant Examiner*—Yong Pak
(74) *Attorney, Agent, or Firm*—Suzanne A. Sprunger; Michael K. Kirschner; Stuart L. Watt

(57) ABSTRACT

The invention is directed to purified and isolated kappa B kinase-related kinases 1 and 2 (IKR-1 and IKR-2) polypeptides and fragments thereof, the nucleic acids encoding such polypeptides, processes for production of recombinant forms of such polypeptides, antibodies generated against these polypeptides, fragmented peptides derived from these polypeptides, and the uses of the above.

23 Claims, 6 Drawing Sheets

NAME:IKR-1

Nucleotide sequence:

```
   1 CACAGGAAAC AGCTATGACC ATGATTACGC CAAGCTCGAA ATTAACCCTC
  51 ACTAAAGGGA ACAAAAGCTG GAGCTCCACC GCGGTGGCGG CCGCTCTAGA
 101 ACTAGTGGAT CCCCCGGGCT GCAGGAATTC CGGCCTGGGA CTGGGTACCC
 151 CACTGCTCTC AGAGAGGCAG GAAAGAGACC TTCAGGCTCA AGACCATCAC
 201 CTGCTTTGCC TGTGGATCCT GGGGGGCCCC ATAGCTACCA GGATCTTCTA
 251 GGCACTGCCC AGGATTGACT TCAAGGCCTG AATCCCTGGG GGTGCCACCC
 301 AGTTCCACAA GTCTGCATTG CCCTGCAACT GAGATAGGAG ATGGGGAAGA
 351 AGATAGCCAA GCCCAGGAGA TGCAGAGTAC CACTAACTAC CTGTGGCATA
 401 CTGATGACCT GCTAGGGCAG GGGGCCACTG CCAGTGTGTA CAAGGCCCGA
 451 AACAAGAAAT CCGGGGAGGT GGTTGCTGTA AAGGTCTTCA ACTCAGCCAG
 501 CTATCGGCGA CCTCCTGAGG TTCAGGTGAG GGAGTTTGAG GTCCTGCGGA
 551 GGCTGAATCA CCAGAACATC GTGAAGCTAT TCGCAGTGGA GGAAACGGGA
 601 GGCAGCCGGC AGAAGGTGCT AATCATGGAG TACTGCTCCA GTGGGAGCCT
 651 GCTGAGCGTG CTGGAAGACC CTGAGAACAC GTTCGGGCTT TCTGAAGAGG
 701 AGTTCCTAGT GGTGCTGCGC TGTGTGGTGG CTGGCATGAA CCACCTGCGG
 751 GAGAATGGCA TTGTCCATCG GGACATCAAA CCTGGGAACA TCATGCGCCT
 801 GGTGGGCGAG GAGGGGCAGA GCATCTATAA GCTGTCTGAC TTCGGGGCTG
 851 CCCGCAAGCT GGACGATGAT GAGAAGTTTG TTTCTGTCTA TGGTACAGAG
 901 GAATACCTGC ACCCTGACAT GTATGAGCGT GCAGTGCTGC GCAAACCCCA
 951 GCAAAAGGCA TTTGGTGTGA CTGTGGATCT CTGGAGTATT GGGGTGACCC
1001 TGTACCACGC AGCCACAGGC AGTCTGCCCT TCATCCCCTT CGGTGGGCCC
1051 CGGCGCAACA AAGAGATCAT GTACAGAATC ACCACAGAGA AGCCAGCCGG
1101 GGCCATTTCA GGGACTCAGA AGCACGAAAA TGGTCCCTTG GAGTGGAGCT
1151 ACAGCCTCCC CATCACCTGT AGACTGTCCA TGGGACTGCA GAACCAGCTG
1201 GTGCCCATCC TGGCCAACAT CCTGGAGGTG GAAGAGGATA AGTGCTGGGG
1251 CTTTGATCAG TTCTTCGCGG AGACCAGTGA CATTCTGCAG CGAACGGTCA
1301 TCCACGTCTT TTCCCTACCC CAGGCCGTTT TGCATCATGT CTACATCCAC
1351 GCCCACAACA CGATTGCCAT CTTTTTGGAG GCTGTATATG AGCAGACCAA
1401 CGTGACCCCC AAACACCAGG AGTACCTCTT CGAGGGTCAC CCTTGTGTCC
1451 TTGAGCCAAG CCTCTCAGCC CAGCACATCG CCCACACAGC TGCCAGCAGC
1501 CCTCTAACTC TGTTCAGCAT GTCCAGCGAC ACACCTAAGG GGCTGGCCTT
1551 CAGGGACCCT GCTCTGGATG TCCCAAAGTT CGTCCCTAAG GTTGACCTAC
1601 AGGCCGATTA CAGCACAGCT AAGGGGGTGC TGGGCGCTGG CTACCAGGCC
1651 CTGTGGCTGG CGCGGGTCCT GCTGGATGGA CAGGCGTTGA TGCTTCGGGG
1701 GTTACATTGG GTCCTGGAGG TGCTTCAGGA CACGTGCCAG CAGACACTGG
1751 AGGTCACACG GACAGCCCTC CTCTACCTCA GCAGCAGCCT GGGCACTGAA
1801 AGGTTCAGCA GTGGACGGGG GATGCCTGAC GTCCAGGAAC GAAAGGAGGC
1851 CACAGAGCTA AGAACCAGGC TGCAGACTCT CTCAGAGATC CTGTCTAAAT
```

```
1901 GTTCCCACAA TGTCACAGAA ACCCAAAGGA GCCTGAGCTG TCTGGGTGAA
1951 GAGCTTTTAA AGAACCGGGA CCAGATTCAT GAGGATAACA AAAGTATCCA
2001 GAAGATTCAG TGTTGTTTGG ACAAGATGCA CTTCATCTAC AAACAGTTCA
2051 AGAAATCCAG GATGAGGCCA GGGCTCAGCT ACAATGAGGA GCAGATCCAC
2101 AAGCTGGATA AGGTAAATTT CAGTCATCTA GCCAAGAGGC TGCTGCAGGT
2151 GTTCCAGGAG GAGTGTGTGC AGACGTATCA GGTGTCGCTG GTCACACACG
2201 GCAAGCGGAT GAGGCAGGTG CAGAGGGCCC AGAACCACCT GCATCTCATT
2251 GGCCACTCTG TGGCCACCTG TAACTCGGAA GCCCGGGGAG CCCAGGAGAG
2301 TCTGAACAAG ATCTTTGATC AGCTCCTTCT GGACAGAGCT TCCGAACAGG
2351 GAGCTGAGGT GTCACCGCAA CCTATGGCTC CTCATCCCGG CCCTGATCCG
2401 AAGGACCTGG TCTTCCACAT GCAGGAGCTT TGTAATGATA TGAAGCTATT
2451 GGCCTTTGAT CTCCAGGACA ACAACCGACT CATCGAACGG TTACATAGAG
2501 TTCCATCGGC ACCAGATGTC TGAGCTCCCT GGGGGTTCAC AAGGCACTCA
2551 GAAGCAATAG AAACATTCAT ATTGTACCCC TACACTGTGA GACCAAATTC
2601 AGGGCAAGTT CTGGTTCCAT CTCACTAGCC TACCTCCCTC TTGGCCATTG
2651 GCCATTGGCC AACAAACTAG CATTACTTTG ACTGTCCTCT TGGGAAGCAG
2701 CTAGGACAGG GACTCCTGGC CATCCCAGGC AGTATCTACA GAAGAGACCA
2751 TGCGGCTACC ACAGCCTTAT CAAGACACCA AGACTGTTCT TCCTCACCCA
2801 GGCTCTGGAG GTCTGGTCTT GGAAAGAAAA GGCTCAGCCC TCTCACGCTC
2851 TGCACTTCCC AGGACCAGCA GGCGTCTCCT GTGGCTTCTC CTGCCTCTCC
2901 AGGGTGCTGG ATCAGAATGC TTATTCTTGG TTGTTTCCTG TGCTGCTTCC
2951 TGAGTGTCCC CATCCCTGGC CTCAGGCAAC CCACAAACGG CCCCTCTGTG
3001 CTTGGTCTAG ATGCACCTGC ATTTGAGAAA GTGGGTGGTT GAGGCTAACT
3051 GCTGGTGCTT TGAGGATTCT CCTTGACCTT TTCTCCGAGG AACGCTTGGT
3101 TCTAAGAAAC AGCTGGTCAG TATCAACCAC AGCCATGCTA ACTGGACAGA
3151 TGTTGGAACC CAAAGTCCTA AGGAGAGAGC AGGCCTGCAC CTTCAGACAT
3201 GGAATAAATA CATCGCCTTT TCTGTTTAAA AAAAAAAAAA AAAAACCGGA
3251 ATTCGATATC AAGCTTATCG ATACCGTCGA CCTCGAGGGG GGGCCCGGTA
3301 CCCAATTCGC CCTATAGTGA GTCGTATTAC AATTCACTGG CCGTCGTTTT
3351 ACAACGTCGT GACTGGGAAA ACCCTGGCGT TACCC    (SEQ ID NO:1)
```

OTHER PUBLICATIONS

Plowman et al., GeneSeq Database Accession No. AAB65601; Mar. 27, 2001.

Nagase, T., et al., "Prediction of the Coding Sequences of Unidentified Human Genes. IV. The Coding Sequences of 40 New Genes (KIAA0121–KIAA0160) Deduced by Analysis of cDNA from Human Cell Line KG–1," *DNA Research*, vol. 2, pp. 167–174 (1995).

Marra, M., et al., "The WashU–HHMI Mouse EST Project," EMBL Database Entry AA867810, Accession No. AA867810, XP002125811 (Mar. 17, 1998) Abstract.

Marra, M., et al., "The WashU–HHMI Mouse EST Project," EMBL Database Entry MMAA65250, Accession No. AA265250, XP002125812 (Mar. 21, 1997) Abstract.

Marra, M., et al., "The WashU–HHMI Mouse EST Project," EMBL Database Entry MMA59563, Accession No. AA059563, XP002125813 (Sep. 24, 1996) Abstract.

Marra, M., et al., "The WashU–HHMI Mouse EST Project," EMBL Database Entry MM1266689, Accession No. AA475369, XP002125814 (Jun. 22, 1997) Abstract.

Marra, M., et al., "The WashU–HHMI Mouse EST Project," EMBL Database Entry AI663156, Accession No. AI663156, XP002125815 (May 11, 1999) Abstract.

Wisniewski, D., et al., "Mus Musculus Homolog of Human T2K cDNA," EMBL Database Entry AF145705, Accession No. AF145705, XP002125816 (Jun. 3, 1999) Abstract.

Pomerantz, J, et al., "NF–kB, TANK and TBK1, a Novel IKK–Related Kinase," EMBL Journal, vol. 18, No. 23, pp. 6694–6704 (1999).

International Search Report—Int'l. Appln. No. PCT/US99/17576.

* cited by examiner

NAME:IKR-1

Nucleotide sequence:

```
   1  CACAGGAAAC AGCTATGACC ATGATTACGC CAAGCTCGAA ATTAACCCTC
  51  ACTAAAGGGA ACAAAAGCTG GAGCTCCACC GCGGTGGCGG CCGCTCTAGA
 101  ACTAGTGGAT CCCCCGGGCT GCAGGAATTC CGGCCTGGGA CTGGGTACCC
 151  CACTGCTCTC AGAGAGGCAG GAAAGAGACC TTCAGGCTCA AGACCATCAC
 201  CTGCTTTGCC TGTGGATCCT GGGGGGCCCC ATAGCTACCA GGATCTTCTA
 251  GGCACTGCCC AGGATTGACT TCAAGGCCTG AATCCCTGGG GGTGCCACCC
 301  AGTTCCACAA GTCTGCATTG CCCTGCAACT GAGATAGGAG ATGGGGAAGA
 351  AGATAGCCAA GCCCAGGAGA TGCAGAGTAC CACTAACTAC CTGTGGCATA
 401  CTGATGACCT GCTAGGGCAG GGGGCCACTG CCAGTGTGTA CAAGGCCCGA
 451  AACAAGAAAT CCGGGGAGGT GGTTGCTGTA AAGGTCTTCA ACTCAGCCAG
 501  CTATCGGCGA CCTCCTGAGG TTCAGGTGAG GGAGTTTGAG GTCCTGCGGA
 551  GGCTGAATCA CCAGAACATC GTGAAGCTAT TCGCAGTGGA GGAAACGGGA
 601  GGCAGCCGGC AGAAGGTGCT AATCATGGAG TACTGCTCCA GTGGGAGCCT
 651  GCTGAGCGTG CTGGAAGACC CTGAGAACAC GTTCGGGCTT TCTGAAGAGG
 701  AGTTCCTAGT GGTGCTGCGC TGTGTGGTGG CTGGCATGAA CCACCTGCGG
 751  GAGAATGGCA TTGTCCATCG GGACATCAAA CCTGGGAACA TCATGCGCCT
 801  GGTGGGCGAG GAGGGGCAGA GCATCTATAA GCTGTCTGAC TTCGGGGCTG
 851  CCCGCAAGCT GGACGATGAT GAGAAGTTTG TTTCTGTCTA TGGTACAGAG
 901  GAATACCTGC ACCCTGACAT GTATGAGCGT GCAGTGCTGC GCAAACCCCA
 951  GCAAAAGGCA TTTGGTGTGA CTGTGGATCT CTGGAGTATT GGGGTGACCC
1001  TGTACCACGC AGCCACAGGC AGTCTGCCCT TCATCCCCTT CGGTGGGCCC
1051  CGGCGCAACA AAGAGATCAT GTACAGAATC ACCACAGAGA AGCCAGCCGG
1101  GGCCATTTCA GGGACTCAGA AGCACGAAAA TGGTCCCTTG GAGTGGAGCT
1151  ACAGCCTCCC CATCACCTGT AGACTGTCCA TGGGACTGCA GAACCAGCTG
1201  GTGCCCATCC TGGCCAACAT CCTGGAGGTG GAAGAGGATA AGTGCTGGGG
1251  CTTTGATCAG TTCTTCGCGG AGACCAGTGA CATTCTGCAG CGAACGGTCA
1301  TCCACGTCTT TTCCCTACCC CAGGCCGTTT TGCATCATGT CTACATCCAC
1351  GCCCACAACA CGATTGCCAT CTTTTTGGAG GCTGTATATG AGCAGACCAA
1401  CGTGACCCCC AAACACCAGG AGTACCTCTT CGAGGGTCAC CCTTGTGTCC
1451  TTGAGCCAAG CCTCTCAGCC CAGCACATCG CCCACACAGC TGCCAGCAGC
1501  CCTCTAACTC TGTTCAGCAT GTCCAGCGAC ACACCTAAGG GGCTGGCCTT
1551  CAGGGACCCT GCTCTGGATG TCCAAAGTT CGTCCCTAAG GTTGACCTAC
1601  AGGCCGATTA CAGCACAGCT AAGGGGGTGC TGGGCGCTGG CTACCAGGCC
1651  CTGTGGCTGG CGCGGGTCCT GCTGGATGGA CAGGCGTTGA TGCTTCGGGG
1701  GTTACATTGG GTCCTGGAGG TGCTTCAGGA CACGTGCCAG CAGACACTGG
1751  AGGTCACACG GACAGCCCTC CTCTACCTCA GCAGCAGCCT GGGCACTGAA
1801  AGGTTCAGCA GTGGAGCGGG GATGCCTGAC GTCCAGGAAC GAAAGGAGGC
1851  CACAGAGCTA AGAACCAGGC TGCAGACTCT CTCAGAGATC CTGTCTAAAT
```

```
1901  GTTCCCACAA TGTCACAGAA ACCCAAAGGA GCCTGAGCTG TCTGGGTGAA
1951  GAGCTTTTAA AGAACCGGGA CCAGATTCAT GAGGATAACA AAAGTATCCA
2001  GAAGATTCAG TGTTGTTTGG ACAAGATGCA CTTCATCTAC AAACAGTTCA
2051  AGAAATCCAG GATGAGGCCA GGGCTCAGCT ACAATGAGGA GCAGATCCAC
2101  AAGCTGGATA AGGTAAATTT CAGTCATCTA GCCAAGAGGC TGCTGCAGGT
2151  GTTCCAGGAG GAGTGTGTGC AGACGTATCA GGTGTCGCTG GTCACACACG
2201  GCAAGCGGAT GAGGCAGGTG CAGAGGGCCC AGAACCACCT GCATCTCATT
2251  GGCCACTCTG TGGCCACCTG TAACTCGGAA GCCCGGGGAG CCCAGGAGAG
2301  TCTGAACAAG ATCTTTGATC AGCTCCTTCT GGACAGAGCT TCCGAACAGG
2351  GAGCTGAGGT GTCACCGCAA CCTATGGCTC CTCATCCCGG CCCTGATCCG
2401  AAGGACCTGG TCTTCCACAT GCAGGAGCTT TGTAATGATA TGAAGCTATT
2451  GGCCTTTGAT CTCCAGGACA CAACCGACT CATCGAACGG TTACATAGAG
2501  TTCCATCGGC ACCAGATGTC TGAGCTCCCT GGGGGTTCAC AAGGCACTCA
2551  GAAGCAATAG AAACATTCAT ATTGTACCCC TACACTGTGA GACCAAATTC
2601  AGGGCAAGTT CTGGTTCCAT CTCACTAGCC TACCTCCCTC TTGGCCATTG
2651  GCCATTGGCC AACAAACTAG CATTACTTTG ACTGTCCTCT TGGGAAGCAG
2701  CTAGGACAGG GACTCCTGGC CATCCCAGGC AGTATCTACA GAAGAGACCA
2751  TGCGGCTACC ACAGCCTTAT CAAGACACCA AGACTGTTCT TCCTCACCCA
2801  GGCTCTGGAG GTCTGGTCTT GGAAAGAAAA GGCTCAGCCC TCTCACGCTC
2851  TGCACTTCCC AGGACCAGCA GGCGTCTCCT GTGGCTTCTC CTGCCTCTCC
2901  AGGGTGCTGG ATCAGAATGC TTATTCTTGG TTGTTTCCTG TGCTGCTTCC
2951  TGAGTGTCCC CATCCCTGGC CTCAGGCAAC CCACAAACGG CCCCTCTGTG
3001  CTTGGTCTAG ATGCACCTGC ATTTGAGAAA GTGGGTGGTT GAGGCTAACT
3051  GCTGGTGCTT TGAGGATTCT CCTTGACCTT TTCTCCGAGG AACGCTTGGT
3101  TCTAAGAAAC AGCTGGTCAG TATCAACCAC AGCCATGCTA ACTGGACAGA
3151  TGTTGGAACC CAAAGTCCTA AGGAGAGAGC AGGCCTGCAC CTTCAGACAT
3201  GGAATAAATA CATCGCCTTT TCTGTTTAAA AAAAAAAAA AAAAACCGGA
3251  ATTCGATATC AAGCTTATCG ATACCGTCGA CCTCGAGGGG GGGCCCGGTA
3301  CCCAATTCGC CCTATAGTGA GTCGTATTAC AATTCACTGG CCGTCGTTTT
3351  ACAACGTCGT GACTGGGAAA ACCCTGGCGT TACCC    (SEQ ID NO:1)
```

Figure 1

NAME:IKR-2
Nucleotide sequence:

```
   1  TTGGGTAACG  CCAGGGTTTT  CCCAGTCACG  ACGTTGTAAA  ACGACGGCCA
  51  GTGAATTGTA  ATACGACTCA  CTATAGGGCG  AATTGGGTAC  CGGGCCCCCC
 101  CTCGAGGTCG  ACGGTATCGA  TAAGCTTGAT  ATCGAATTCC  GGCACTCGCG
 151  GGCATACATG  CAAATCTCTT  CTTCCCCCTT  ATCGTGAGGA  GAAGCGCCTG
 201  GACAAGCCGA  GATGCAGAGC  ACCTCCAACC  ATCTGTGGCT  CCTGTCTGAT
 251  ATCCTAGGCC  AGGGGGCCAC  TGCAAATGTC  TTCCGAGGAA  GGCATAAGAA
 301  AACTGGTGAT  CTCTATGCTG  TCAAAGTATT  TAATAACATA  AGCTTCCTTC
 351  GCCCAGTGGA  TGTTCAAATG  AGAGAATTTG  AAGTGTTAAA  AAAACTCAAT
 401  CACAAAAACA  TTGTCAAGTT  ATTTGCTATT  GAAGAGGAGA  CAACAACAAG
 451  ACATAAAGTG  CTTATTATGG  AGTTTTGTCC  CTGTGGGAGT  TTATACACTG
 501  TTCTAGAGGA  GCCGTCCAAT  GCGTATGGAC  TTCCAGAATC  AGAATTTCTC
 551  ATTGTCTTAC  GAGATGTGGT  GGGCGGGATG  AATCATCTCC  GAGAGAACGG
 601  CATAGTGCAC  CGAGATATCA  AGCCAGGCAA  CATCATGCGC  GTCATAGGGG
 651  AGGACGGCCA  GTCTGTGTAC  AAACTCACGG  ATTTCGGCGC  CGCTCGAGAG
 701  CTGGAGGACG  ATGAGCAGTT  TGTGTCTCTG  TACGGCACAG  AAGAGTACCT
 751  GCATCCGGAC  ATGTATGAAA  GGGCAGTGCT  AAGAAAGGAC  CATCAGAAGA
 801  AGTACGGGGC  TACCGTTGAT  CTGTGGAGTG  TTGGAGTGAC  ATTCTACCAT
 851  GCAGCCACGG  GGTCGCTGCC  GTTTAGACCC  TTCGAGGGGC  CTCGGAGGAA
 901  CAAAGAAGTA  ATGTATAAAA  TAATCACTGG  AAGCCGTCT  GGTGCAATAT
 951  CTGGAGTACA  GAAAGCAGAA  AACGGACCAA  TTGACTGGAG  TGGAGACATG
1001  CCTCTCTCCT  GTAGTCTTTC  TCAGGGTCTT  CAGGCACTGC  TTACCCCAGT
1051  TCTTGCAAAC  ATACTTGAAG  CTGATCAGGA  GAAGTGCTGG  GGTTTTGACC
1101  AGTTCTTTGC  AGAGACCAGT  GATGTGCTTC  ACCGAATGGT  GATCCATGTC
1151  TTCTCGCTAC  AACACATGAC  GGCGCATAAG  ATTTACATTC  ACAGCTATAA
1201  CACTGCTGCT  GTGTTCCATG  AACTGGTCTA  TAAACAAACC  AAGATTGTTT
1251  CCTCAAATCA  GAACTTATC  TACGAAGGAC  GACGCTTAGT  CCTAGAACTC
1301  GGACGACTAG  CCCAGCATTT  TCCTAAAACC  ACAGAGGAAA  ATCCTATCTT
1351  TGTCACGAGC  CGGGAACAAC  TCAATACCGT  AGGACTGAGA  TATGAAAAAA
1401  TTTCCCTCCC  TAAAATACAT  CCACGCTATG  ATCTGGATGG  GGACGCCAGC
1451  ATGGCCAAGG  CAGTGACGGG  GGTTGTGTGC  TACGCCTGCA  GAACTGCCAG
1501  TACCCTGCTG  CTCTATCAAG  AATTAATGCG  AAAGGGGGTA  CGGTGGCTGG
1551  TTGAACTGGT  TAAGGATGAT  TACAACGAGA  CCGTCCACAA  GAAGACGGAG
1601  GTAGTGATCA  CACTGGATTT  CTGCATCAGG  AACATTGAGA  AGACTGTGAA
1651  AGTGTATGAG  AAGTTGATGA  AGGTCAACCT  GGAAGCCGCA  GAGCTGGGTG
1701  AGATTTCAGA  CATACACACC  AAGCTGCTGA  GACTTTCCAG  TTCTCAGGGA
1751  ACAATAGAAA  GCAGTCTTCA  GGACATCAGC  AGCAGGCTGT  CTCCAGGGGG
1801  CTTGCTGGCC  GACACCTGGG  CACATCAAGA  AGGCACGCAT  CCAAGAGACA
1851  GGAATGTAGA  AAAACTGCAG  GTCCTGTTGA  ACTGCATCAC  AGAGATTTAC
1901  TATCAGTTCA  AAAAGACAA  AGCAGAACGC  AGACTAGCTT  ATAATGAAGA
```

```
1951  ACAGATCCAC  AAATTTGATA  AGCAAAAATT  GTATTACCAT  GCCACAAAAG
2001  CAATGAGCCA  CTTCTCAGAA  GAATGTGTTA  GAAAGTATGA  AGCGTTTAAA
2051  GATAAGTCGG  AAGAGTGGAT  GAGAAAGATG  CTTCATCTTA  GGAAGCAGCT
2101  GTTATCGCTA  ACTAATCAGT  GTTTCGATAT  CGAAGAGGAA  GTGTCCAAGT
2151  ATCAAGACTA  TACTAACGAG  TTACAAGAAA  CTCTGCCTCA  GAAAATGCTC
2201  GCAGCCTCCG  GCGGCGTCAA  GCACGCCATG  GCCCCGATCT  ACCCCAGCTC
2251  TAACACCTTA  GTGGAGATGA  CTCTTGGTAT  GAAGAAGTTA  AAGGAGGAGA
2301  TGGAAGGCGT  GGTTAAGGAG  CTGGCCGAGA  ACAATCATAT  TTTAGAAAGG
2351  TTTGGGTCTT  TAACAATGGA  TGGTGGCCTT  CGCAATGTGG  ACTGTCTTTA
2401  GCTTCCTAGG  GAGTCTGGGA  AGTTCTAGTT  TGCACAAGAA  GATAACACTG
2451  GGGCACGAAA  TGAACACCTT  TGTGAATGGA  GTTCTTATTT  CTACACTTCA
2501  GTATTTGATG  AGGTCATGTA  AATATGTACA  GTTTGTAAAT  ACATATACAT
2551  ATATATATAT  ATATATGAAT  TTTGGCTGCT  GTAACAAAGA  CAGATTGACC
2601  TCAGCGAGCT  GTAGAAGAAA  GCCATGACCA  GCCAGTGCTT  TGGGGTGCTC
2651  TCCCTAATTC  TTCACATAAG  GCTGGAGAAA  TCAATTGCTT  GGTGCCTAAA
2701  GAAAGTATTT  TTTGAATTGG  CATTCTTAAA  ATTTTGAAAG  GACTGATAGT
2751  CGACACAGTG  TAACTGGAGG  AGACACAGGG  CTTTGTGACG  GGAACAGAAC
2801  CGCGGTTTAA  CCACAGTCGG  TTCCCTGACA  AGGATAAAGT  GGCATTATCT
2851  CATTTGACCG  GGTGCCCAAA  TCTCAGTTTT  CCTCGGATGT  TTGATTTTAG
2901  GTGAATTATT  GAGCAAAAC   TTTAAAGTGA  ATTCATTGTT  TAAACTATTC
2951  ATTTTTCCTT  TGGTCATGAA  TGTGTAATTG  TCATTCAGAT  CCTAGTATCA
3001  TTTCAATTGT  CTTAAGATGT  ATATTTCTGT  ACTTTAATTC  TGCTATTTCA
3051  TGAAAAAATA  AATTTCTCCC  GGAATTCCTG  CAGCCCGGGG  GATCCACTAG
3101  TTCTAGAGCG  GCCGCCACCG  CGGTGGAGCT  CCAGCTTTTG  TTCCCTTTAG
3151  TGAGGGTTAA  TTTCGAGCTT  GGCGTAATCA  TGGTCATAGC  TGTTTCCTGT
3201  GTGAAATTGT  TATCCGCTC       (SEQ ID NO:3)
```

Figure 2

Name: IKR-1 (Polypeptide)

```
  1  MQSTTNYLWH  TDDLLGQGAT  ASVYKARNKK  SGEVVAVKVF  NSASYRRPPE
 51  VQVREFEVLR  RLNHQNIVKL  FAVEETGGSR  QKVLIMEYCS  SGSLLSVLED
101  PENTFGLSEE  EFLVVLRCVV  AGMNHLRENG  IVHRDIKPGN  IMRLVGEEGQ
151  SIYKLSDFGA  ARKLDDDEKF  VSVYGTEEYL  HPDMYERAVL  RKPQQKAFGV
201  TVDLWSIGVT  LYHAATGSLP  FIPFGGPRRN  KEIMYRITTE  KPAGAISGTQ
251  KHENGPLEWS  YSLPITCRLS  MGLQNQLVPI  LANILEVEED  KCWGFDQFFA
301  ETSDILQRTV  IHVFSLPQAV  LHHVYIHAHN  TIAIFLEAVY  EQTNVTPKHQ
351  EYLFEGHPCV  LEPSLSAQHI  AHTAASSPLT  LFSMSSDTPK  GLAFRDPALD
401  VPKFVPKVDL  QADYSTAKGV  LGAGYQALWL  ARVLLDGQAL  MLRGLHWVLE
451  VLQDTCQQTL  EVTRTALLYL  SSSLGTERFS  SGAGMPDVQE  RKEATELRTR
501  LQTLSEILSK  CSHNVTETQR  SLSCLGEELL  KNRDQIHEDN  KSIQKIQCCL
551  DKMHFIYKQF  KKSRMRPGLS  YNEEQIHKLD  KVNFSHLAKR  LLQVFQEECV
601  QTYQVSLVTH  GKRMRQVQRA  QNHLHLIGHS  VATCNSEARG  AQESLNKIFD
651  QLLLDRASEQ  GAEVSPQPMA  PHPGPDPKDL  VFHMQELCND  MKLLAFDLQD
701  NNRLIERLHR  VPSAPDV     (SEQ ID NO:2)
```

Figure 3

Name:IKR-2 (Polypeptide)

```
  1  MQSTSNHLWL  LSDILGQGAT  ANVFRGRHKK  TGDLYAVKVF  NNISFLRPVD
 51  VQMREFEVLK  KLNHKNIVKL  FAIEEETTTR  HKVLIMEFCP  CGSLYTVLEE
101  PSNAYGLPES  EFLIVLRDVV  GGMNHLRENG  IVHRDIKPGN  IMRVIGEDGQ
151  SVYKLTDFGA  ARELEDDEQF  VSLYGTEEYL  HPDMYERAVL  RKDHQKKYGA
201  TVDLWSVGVT  FYHAATGSLP  FRPFEGPRRN  KEVMYKIITG  KPSGAISGVQ
251  KAENGPIDWS  GDMPLSCSLS  QGLQALLTPV  LANILEADQE  KCWGFDQFFA
301  ETSDVLHRMV  IHVFSLQHMT  AHKIYIHSYN  TAAVFHELVY  KQTKIVSSNQ
351  ELIYEGRRLV  LELGRLAQHF  PKTTEENPIF  VTSREQLNTV  GLRYEKISLP
401  KIHPRYDLDG  DASMAKAVTG  VVCYACRTAS  TLLLYQELMR  KGVRWLVELV
451  KDDYNETVHK  KTEVVITLDF  CIRNIEKTVK  VYEKLMKVNL  EAAELGEISD
501  IHTKLLRLSS  SQGTIESSLQ  DISSRLSPGG  LLADTWAHQE  GTHPRDRNVE
551  KLQVLLNCIT  EIYYQFKKDK  AERRLAYNEE  QIHKFDKQKL  YYHATKAMSH
601  FSEECVRKYE  AFKDKSEEWM  RKMLHLRKQL  LSLTNQCFDI  EEEVSKYQDY
651  TNELQETLPQ  KMLAASGGVK  HAMAPIYPSS  NTLVEMTLGM  KKLKEEMEGV
701  VKELAENNHI  LERFGSLTMD  GGLRNVDCL   (SEQ ID NO: 4)
```

Figure 4

SEQUENCE LISTING

<160> NUMBER OF SEQ ID NOS: 4

<210> SEQ ID NO 1
<211> LENGTH: 3385
<212> TYPE: DNA
<213> ORGANISM: murine

<400> SEQUENCE: 1

| | | | | | | |
|---|---|---|---|---|---|---|
| cacaggaaac | agctatgacc | atgattacgc | caagctcgaa | attaaccctc | actaaaggga | 60 |
| acaaaagctg | gagctccacc | gcggtggcgg | ccgctctaga | actagtggat | cccccgggct | 120 |
| gcaggaattc | cggcctggga | ctgggtaccc | cactgctctc | agagaggcag | gaaagagacc | 180 |
| ttcaggctca | agaccatcac | ctgctttgcc | tgtggatcct | gggggccccc | atagctacca | 240 |
| ggatcttcta | ggcactgccc | aggattgact | tcaaggcctg | aatccctggg | ggtgccaccc | 300 |
| agttccacaa | gtctgcattg | ccctgcaact | gagataggag | atgggaaga | agatagccaa | 360 |
| gcccaggaga | tgcagagtac | cactaactac | ctgtggcata | ctgatgacct | gctagggcag | 420 |
| ggggccactg | ccagtgtgta | caaggcccga | aacaagaaat | ccggggaggt | ggttgctgta | 480 |
| aaggtcttca | actcagccag | ctatcggcga | cctcctgagg | ttcaggtgag | ggagtttgag | 540 |
| gtcctgcgga | ggctgaatca | ccagaacatc | gtgaagctat | tcgcagtgga | ggaaacggga | 600 |
| ggcagccggc | agaaggtgct | aatcatggag | tactgctcca | gtgggagcct | gctgagcgtg | 660 |
| ctggaagacc | ctgagaacac | gttcgggctt | tctgaagagg | agttcctagt | ggtgctgcgc | 720 |
| tgtgtggtgg | ctggcatgaa | ccacctgcgg | gagaatggca | ttgtccatcg | ggacatcaaa | 780 |
| cctgggaaca | tcatgcgcct | ggtgggcgag | gaggggcaga | gcatctataa | gctgtctgac | 840 |
| ttcggggctg | cccgcaagct | ggacgatgat | gagaagtttg | tttctgtcta | tggtacagag | 900 |
| gaatacctgc | accctgacat | gtatgagcgt | gcagtgctgc | gcaaacccca | gcaaaaggca | 960 |
| tttggtgtga | ctgtggatct | ctggagtatt | ggggtgaccc | tgtaccacgc | agccacaggc | 1020 |
| agtctgccct | tcatcccctt | cggtgggccc | cggcgcaaca | aagagatcat | gtacagaatc | 1080 |
| accacagaga | agccagccgg | ggccatttca | gggactcaga | agcacgaaaa | tggtcccttg | 1140 |
| gagtggagct | acagcctccc | catcacctgt | agactgtcca | tgggactgca | gaaccagctg | 1200 |
| gtgcccatcc | tggccaacat | cctggaggtg | gaagaggata | agtgctgggg | ctttgatcag | 1260 |
| ttcttcgcgg | agaccagtga | cattctgcag | cgaacggtca | tccacgtctt | ttccctaccc | 1320 |
| caggccgttt | tgcatcatgt | ctacatccac | gcccacaaca | cgattgccat | cttttggag | 1380 |
| gctgtatatg | agcagaccaa | cgtgaccccc | aaacaccagg | agtacctctt | cgagggtcac | 1440 |
| ccttgtgtcc | ttgagccaag | cctctcagcc | cagcacatcg | cccacacagc | tgccagcagc | 1500 |
| cctctaactc | tgttcagcat | gtccagcgac | acacctaagg | ggctggcctt | cagggaccct | 1560 |
| gctctggatg | tcccaaagtt | cgtccctaag | gttgacctac | aggccgatta | cagcacagct | 1620 |
| aaggggggtgc | tgggcgctgg | ctaccaggcc | ctgtggctgg | cgcgggtcct | gctggatgga | 1680 |
| caggcgttga | tgcttcgggg | gttacattgg | gtcctggagg | tgcttcagga | cacgtgccag | 1740 |
| cagacactgg | aggtcacacg | gacagccctc | ctctacctca | gcagcagcct | gggcactgaa | 1800 |
| aggttcagca | gtggagcggg | gatgcctgac | gtccaggaac | gaaaggaggc | cacagagcta | 1860 |

-continued

```
agaaccaggc tgcagactct ctcagagatc ctgtctaaat gttcccacaa tgtcacagaa      1920
acccaaagga gcctgagctg tctgggtgaa gagcttttaa agaaccggga ccagattcat      1980
gaggataaca aaagtatcca gaagattcag tgttgtttgg acaagatgca cttcatctac      2040
aaacagttca agaaatccag gatgaggcca gggctcagct acaatgagga gcagatccac      2100
aagctggata aggtaaattt cagtcatcta gccaagaggc tgctgcaggt gttccaggag      2160
gagtgtgtgc agacgtatca ggtgtcgctg gtcacacacg gcaagcggat gaggcaggtg      2220
cagagggccc agaaccacct gcatctcatt ggccactctg tggccacctg taactcggaa      2280
gcccggggag cccaggagag tctgaacaag atctttgatc agctccttct ggacagagct      2340
tccgaacagg gagctgaggt gtcaccgcaa cctatggctc ctcatcccgg ccctgatccg      2400
aaggacctgg tcttccacat gcaggagctt tgtaatgata tgaagctatt ggcctttgat      2460
ctccaggaca caaccgact catcgaacgg ttacatagag ttccatcggc accagatgtc      2520
tgagctccct gggggttcac aaggcactca gaagcaatag aaacattcat attgtacccc      2580
tacactgtga gaccaaattc agggcaagtt ctggttccat ctcactagcc tacctccctc      2640
ttggccattg gccattggcc aacaaactag cattactttg actgtcctct gggaagcag       2700 ctaggacagg gactcctggc catcccaggc agtatctaca gaagagacca tgcggctacc      2760
acagccttat caagacacca agactgttct tcctcaccca ggctctggag gtctggtctt      2820
ggaaagaaaa ggctcagccc tctcacgctc tgcacttccc aggaccagca ggcgtctcct      2880
gtggcttctc ctgcctctcc agggtgctgg atcagaatgc ttattcttgg ttgtttcctg      2940
tgctgcttcc tgagtgtccc catccctggc tcaggcaac ccacaaacgg ccctctgtg       3000 cttggtctag atgcacctgc atttgagaaa gtgggtggtt gaggctaact gctggtgctt      3060
tgaggattct ccttgacctt ttctccgagg aacgcttggt tctaagaaac agctggtcag      3120
tatcaaccac agccatgcta actggacaga tgttggaacc caaagtccta aggagagagc      3180
aggcctgcac cttcagacat ggaataaata catcgccttt tctgttaaa aaaaaaaaa       3240 aaaaaccgga attcgatatc aagcttatcg ataccgtcga cctcgagggg gggcccggta      3300
cccaattcgc cctatagtga gtcgtattac aattcactgg ccgtcgtttt acaacgtcgt      3360
gactgggaaa accctggcgt taccc                                           3385
```

<210> SEQ ID NO 2
<211> LENGTH: 717
<212> TYPE: PRT
<213> ORGANISM: murine

<400> SEQUENCE: 2

```
Met Gln Ser Thr Thr Asn Tyr Leu Trp His Thr Asp Asp Leu Leu Gly
  1               5                  10                  15

Gln Gly Ala Thr Ala Ser Val Tyr Lys Ala Arg Asn Lys Lys Ser Gly
                 20                  25                  30

Glu Val Val Ala Val Lys Val Phe Asn Ser Ala Ser Tyr Arg Arg Pro
             35                  40                  45

Pro Glu Val Gln Val Arg Glu Phe Glu Val Leu Arg Arg Leu Asn His
         50                  55                  60

Gln Asn Ile Val Lys Leu Phe Ala Val Glu Glu Thr Gly Gly Ser Arg
 65                  70                  75                  80

Gln Lys Val Leu Ile Met Glu Tyr Cys Ser Ser Gly Ser Leu Leu Ser
                 85                  90                  95
```

```
-continued

Val Leu Glu Asp Pro Glu Asn Thr Phe Gly Leu Ser Glu Glu Phe
            100                 105                 110

Leu Val Val Leu Arg Cys Val Ala Gly Met Asn His Leu Arg Glu
            115                 120                 125

Asn Gly Ile Val His Arg Asp Ile Lys Pro Gly Asn Ile Met Arg Leu
            130                 135                 140

Val Gly Glu Glu Gly Gln Ser Ile Tyr Lys Leu Ser Asp Phe Gly Ala
145                 150                 155                 160

Ala Arg Lys Leu Asp Asp Asp Glu Lys Phe Val Ser Val Tyr Gly Thr
                165                 170                 175

Glu Glu Tyr Leu His Pro Asp Met Tyr Glu Arg Ala Val Leu Arg Lys
                180                 185                 190

Pro Gln Lys Ala Phe Gly Val Thr Val Asp Leu Trp Ser Ile Gly
            195                 200                 205

Val Thr Leu Tyr His Ala Ala Thr Gly Ser Leu Pro Phe Ile Pro Phe
            210                 215                 220

Gly Gly Pro Arg Arg Asn Lys Glu Ile Met Tyr Arg Ile Thr Thr Glu
225                 230                 235                 240

Lys Pro Ala Gly Ala Ile Ser Gly Thr Gln Lys His Glu Asn Gly Pro
                245                 250                 255

Leu Glu Trp Ser Tyr Ser Leu Pro Ile Thr Cys Arg Leu Ser Met Gly
            260                 265                 270

Leu Gln Asn Gln Leu Val Pro Ile Leu Ala Asn Ile Leu Glu Val Glu
            275                 280                 285

Glu Asp Lys Cys Trp Gly Phe Asp Gln Phe Phe Ala Glu Thr Ser Asp
290                 295                 300

Ile Leu Gln Arg Thr Val Ile His Val Phe Ser Leu Pro Gln Ala Val
305                 310                 315                 320

Leu His His Val Tyr Ile His Ala His Asn Thr Ile Ala Ile Phe Leu
            325                 330                 335

Glu Ala Val Tyr Glu Gln Thr Asn Val Thr Pro Lys His Gln Glu Tyr
            340                 345                 350

Leu Phe Glu Gly His Pro Cys Val Leu Glu Pro Ser Leu Ser Ala Gln
            355                 360                 365

His Ile Ala His Thr Ala Ala Ser Ser Pro Leu Thr Leu Phe Ser Met
            370                 375                 380

Ser Ser Asp Thr Pro Lys Gly Leu Ala Phe Arg Asp Pro Ala Leu Asp
385                 390                 395                 400

Val Pro Lys Phe Val Pro Lys Val Asp Leu Gln Ala Asp Tyr Ser Thr
                405                 410                 415

Ala Lys Gly Val Leu Gly Ala Gly Tyr Gln Ala Leu Trp Leu Ala Arg
            420                 425                 430

Val Leu Leu Asp Gly Gln Ala Leu Met Leu Arg Gly Leu His Trp Val
            435                 440                 445

Leu Glu Val Leu Gln Asp Thr Cys Gln Gln Thr Leu Glu Val Thr Arg
            450                 455                 460

Thr Ala Leu Leu Tyr Leu Ser Ser Ser Leu Gly Thr Glu Arg Phe Ser
465                 470                 475                 480

Ser Gly Ala Gly Met Pro Asp Val Gln Glu Arg Lys Glu Ala Thr Glu
                485                 490                 495

Leu Arg Thr Arg Leu Gln Thr Leu Ser Glu Ile Leu Ser Lys Cys Ser
            500                 505                 510

His Asn Val Thr Glu Thr Gln Arg Ser Leu Ser Cys Leu Gly Glu Glu
```

|        |        |        |        |        |        |        |        |        |        |        |        |
|--------|--------|--------|--------|--------|--------|--------|--------|--------|--------|--------|--------|
|        | 515    |        |        |        | 520    |        |        |        | 525    |        |        |
| Leu    | Leu    | Lys    | Asn    | Arg    | Asp    | Gln    | Ile    | His    | Glu    | Asp    | Asn    | Lys | Ser | Ile | Gln |
|        |        |        | 530    |        |        |        |        | 535    |        |        |        | 540 |
| Lys    | Ile    | Gln    | Cys    | Cys    | Leu    | Asp    | Lys    | Met    | His    | Phe    | Ile    | Tyr | Lys | Gln | Phe |
| 545    |        |        |        |        | 550    |        |        |        |        | 555    |        |     |     |     | 560 |

Lys Lys Ser Arg Met Arg Pro Gly Leu Ser Tyr Asn Glu Glu Gln Ile
              565                 570                 575

His Lys Leu Asp Lys Val Asn Phe Ser His Leu Ala Lys Arg Leu Leu
            580                 585                 590

Gln Val Phe Gln Glu Glu Cys Val Gln Thr Tyr Gln Val Ser Leu Val
          595                 600                 605

Thr His Gly Lys Arg Met Arg Gln Val Gln Arg Ala Gln Asn His Leu
        610                 615                 620

His Leu Ile Gly His Ser Val Ala Thr Cys Asn Ser Glu Ala Arg Gly
625                 630                 635                 640

Ala Gln Glu Ser Leu Asn Lys Ile Phe Asp Gln Leu Leu Leu Asp Arg
                645                 650                 655

Ala Ser Glu Gln Gly Ala Glu Val Ser Pro Gln Pro Met Ala Pro His
              660                 665                 670

Pro Gly Pro Asp Pro Lys Asp Leu Val Phe His Met Gln Glu Leu Cys
            675                 680                 685

Asn Asp Met Lys Leu Leu Ala Phe Asp Leu Gln Asp Asn Asn Arg Leu
          690                 695                 700

Ile Glu Arg Leu His Arg Val Pro Ser Ala Pro Asp Val
705                 710                 715

<210> SEQ ID NO 3
<211> LENGTH: 3219
<212> TYPE: DNA
<213> ORGANISM: murine

<400> SEQUENCE: 3

```
ttgggtaacg ccagggtttt cccagtcacg acgttgtaaa acgacggcca gtgaattgta    60
atacgactca ctatagggcg aattgggtac cgggcccccc ctcgaggtcg acggtatcga   120
taagcttgat atcgaattcc ggcactcgcg ggcatacatg caaatctctt cttcccccctt   180
atcgtgagga gaagcgcctg gacaagccga gatgcagagc acctccaacc atctgtggct   240
cctgtctgat atcctaggcc aggggccact gcaaatgtc ttccgaggaa ggcataagaa   300
aactggtgat ctctatgctg tcaaagtatt taataacata gcttccttc gcccagtgga   360
tgttcaaatg agagaatttg aagtgttaaa aaaactcaat cacaaaaaca ttgtcaagtt   420
atttgctatt gaagaggaga caacaacaag acataaagtg cttattatgg agttttgtcc   480
ctgtgggagt ttatacactg ttctagagga gccgtccaat gcgtatggac ttccagaatc   540
agaatttctc attgtcttac agatgtggt gggcgggatg aatcatctcc gagagaacgg   600
catagtgcac cgagatatca agccaggcaa catcatgcgc gtcataggg aggacggcca   660
gtctgtgtac aaactcacgg atttcggcgc cgctcgagag ctggaggacg atgagcagtt   720
tgtgtctctg tacggcacag aagagtacct gcatccggac atgtatgaaa gggcagtgct   780
aagaaaggac catcagaaga gtacggggc taccgttgat ctgtggagtg ttggagtgac   840
attctaccat gcagccacgg ggtcgctgcc gtttagaccc ttcgagggc ctcggaggaa   900
caaagaagta atgtataaaa taatcactgg gaagccgtct ggtgcaatat ctggagtaca   960
gaaagcagaa aacggaccaa ttgactggag tgagacatg cctctctcct gtagtctttc  1020
```

-continued

```
tcagggtctt caggcactgc ttaccccagt tcttgcaaac atacttgaag ctgatcagga    1080
gaagtgctgg ggttttgacc agttctttgc agagaccagt gatgtgcttc accgaatggt    1140
gatccatgtc ttctcgctac aacacatgac ggcgcataag atttacattc acagctataa    1200
cactgctgct gtgttccatg aactggtcta taaacaaacc aagattgttt cctcaaatca    1260
agaacttatc tacgaaggac gacgcttagt cctagaactc ggacgactag cccagcattt    1320
tcctaaaacc acagaggaaa atcctatctt tgtcacgagc cgggaacaac tcaataccgt    1380
aggactgaga tatgaaaaaa tttccctccc taaaatacat ccacgctatg atctggatgg    1440
ggacgccagc atggccaagg cagtgacggg ggttgtgtgc tacgcctgca gaactgccag    1500
taccctgctg ctctatcaag aattaatgcg aaagggggta cggtggctgg ttgaactggt    1560
taaggatgat tacaacgaga ccgtccacaa gaagacggag gtagtgatca cactggattt    1620
ctgcatcagg aacattgaga agactgtgaa agtgtatgag aagttgatga aggtcaacct    1680
ggaagccgca gagctgggtg agatttcaga catacacacc aagctgctga acttcccag    1740 ttctcaggga acaatagaaa gcagtcttca ggacatcagc agcaggctgt ctccaggggg    1800
cttgctggcc gacacctggg cacatcaaga aggcacgcat ccaagagaca ggaatgtaga    1860
aaaactgcag gtcctgttga actgcatcac agagatttac tatcagttca aaaaagacaa    1920
agcagaacgc agactagctt ataatgaaga acagatccac aaatttgata gcaaaaatt    1980 gtattaccat gccacaaaag caatgagcca cttctcagaa gaatgtgtta gaaagtatga    2040
agcgtttaaa gataagtcgg aagagtggat gagaaagatg cttcatctta ggaagcagct    2100
gttatcgcta actaatcagt gtttcgatat cgaagaggaa gtgtccaagt atcaagacta    2160
tactaacgag ttacaagaaa ctctgcctca gaaaatgctc gcagcctccg gcggcgtcaa    2220
gcacgccatg gccccgatct accccagctc taacaccta gtggagatga ctcttggtat    2280
gaagaagtta aaggaggaga tggaaggcgt ggttaaggag ctggccgaga caatcatat    2340 tttagaaagg tttgggtctt taacaatgga tggtggcctt cgcaatgtgg actgtcttta    2400
gcttcctagg gagtctggga agttctagtt tgcacaagaa gataacactg gggcacgaaa    2460
tgaacacctt tgtgaatgga gttcttattt ctacacttca gtatttgatg aggtcatgta    2520
aatatgtaca gtttgtaaat acatatacat atatatatat atatatgaat tttggctgct    2580
gtaacaaaga cagattgacc tcagcgagct gtagaagaaa gccatgacca gccagtgctt    2640
tggggtgctc tccctaattc ttcacataag gctggagaaa tcaattgctt ggtgcctaaa    2700
gaaagtattt tttgaattgg cattcttaaa attttgaaag gactgatagt cgacacagtg    2760
taactggagg agacacaggg ctttgtgacg ggaacagaac cgcggtttaa ccacagtcgg    2820
ttccctgaca aggataaagt ggcattatct catttgaccg ggtgcccaaa tctcagtttt    2880
cctcggatgt ttgattttag gtgaattatt gagcaaaaac tttaaagtga attcattgtt    2940
taaactattc atttttcctt tggtcatgaa tgtgtaattg tcattcagat cctagtatca    3000
tttcaattgt cttaagatgt atatttctgt actttaattc tgctatttca tgaaaaaata    3060
aatttctccc ggaattcctg cagcccgggg gatccactag ttctagagcg gccgccaccg    3120
cggtggagct ccagcttttg ttcccttag tgagggttaa tttcgagctt ggcgtaatca    3180
tggtcatagc tgtttcctgt gtgaaattgt tatccgctc                           3219
```

<210> SEQ ID NO 4
<211> LENGTH: 729
<212> TYPE: PRT

-continued

<213> ORGANISM: murine

<400> SEQUENCE: 4

Met Gln Ser Thr Ser Asn His Leu Trp Leu Leu Ser Asp Ile Leu Gly
 1               5                  10                  15
Gln Gly Ala Thr Ala Asn Val Phe Arg Gly Arg His Lys Lys Thr Gly
            20                  25                  30
Asp Leu Tyr Ala Val Lys Val Phe Asn Asn Ile Ser Phe Leu Arg Pro
        35                  40                  45
Val Asp Val Gln Met Arg Glu Phe Glu Val Leu Lys Lys Leu Asn His
    50                  55                  60
Lys Asn Ile Val Lys Leu Phe Ala Ile Glu Glu Thr Thr Thr Arg
65                  70                  75                  80
His Lys Val Leu Ile Met Glu Phe Cys Pro Cys Gly Ser Leu Tyr Thr
                85                  90                  95
Val Leu Glu Glu Pro Ser Asn Ala Tyr Gly Leu Pro Glu Ser Glu Phe
            100                 105                 110
Leu Ile Val Leu Arg Asp Val Val Gly Gly Met Asn His Leu Arg Glu
        115                 120                 125
Asn Gly Ile Val His Arg Asp Ile Lys Pro Gly Asn Ile Met Arg Val
    130                 135                 140
Ile Gly Glu Asp Gly Gln Ser Val Tyr Lys Leu Thr Asp Phe Gly Ala
145                 150                 155                 160
Ala Arg Glu Leu Glu Asp Asp Glu Gln Phe Val Ser Leu Tyr Gly Thr
                165                 170                 175
Glu Glu Tyr Leu His Pro Asp Met Tyr Glu Arg Ala Val Leu Arg Lys
            180                 185                 190
Asp His Gln Lys Lys Tyr Gly Ala Thr Val Asp Leu Trp Ser Val Gly
        195                 200                 205
Val Thr Phe Tyr His Ala Ala Thr Gly Ser Leu Pro Phe Arg Pro Phe
    210                 215                 220
Glu Gly Pro Arg Arg Asn Lys Glu Val Met Tyr Lys Ile Ile Thr Gly
225                 230                 235                 240
Lys Pro Ser Gly Ala Ile Ser Gly Val Gln Lys Ala Glu Asn Gly Pro
                245                 250                 255
Ile Asp Trp Ser Gly Asp Met Pro Leu Ser Cys Ser Leu Ser Gln Gly
            260                 265                 270
Leu Gln Ala Leu Leu Thr Pro Val Leu Ala Asn Ile Leu Glu Ala Asp
        275                 280                 285
Gln Glu Lys Cys Trp Gly Phe Asp Gln Phe Phe Ala Glu Thr Ser Asp
    290                 295                 300
Val Leu His Arg Met Val Ile His Val Phe Ser Leu Gln His Met Thr
305                 310                 315                 320
Ala His Lys Ile Tyr Ile His Ser Tyr Asn Thr Ala Ala Val Phe His
                325                 330                 335
Glu Leu Val Tyr Lys Gln Thr Lys Ile Val Ser Ser Asn Gln Glu Leu
            340                 345                 350
Ile Tyr Glu Gly Arg Arg Leu Val Leu Glu Leu Gly Arg Leu Ala Gln
        355                 360                 365
His Phe Pro Lys Thr Thr Glu Glu Asn Pro Ile Phe Val Thr Ser Arg
    370                 375                 380
Glu Gln Leu Asn Thr Val Gly Leu Arg Tyr Glu Lys Ile Ser Leu Pro
385                 390                 395                 400

```
Lys Ile His Pro Arg Tyr Asp Leu Asp Gly Asp Ala Ser Met Ala Lys
            405                 410                 415

Ala Val Thr Gly Val Val Cys Tyr Ala Cys Arg Thr Ala Ser Thr Leu
            420                 425                 430

Leu Leu Tyr Gln Glu Leu Met Arg Lys Gly Val Arg Trp Leu Val Glu
            435                 440                 445

Leu Val Lys Asp Asp Tyr Asn Glu Thr Val His Lys Lys Thr Glu Val
        450                 455                 460

Val Ile Thr Leu Asp Phe Cys Ile Arg Asn Ile Glu Lys Thr Val Lys
465                 470                 475                 480

Val Tyr Glu Lys Leu Met Lys Val Asn Leu Glu Ala Ala Glu Leu Gly
            485                 490                 495

Glu Ile Ser Asp Ile His Thr Lys Leu Leu Arg Leu Ser Ser Ser Gln
            500                 505                 510

Gly Thr Ile Glu Ser Ser Leu Gln Asp Ile Ser Ser Arg Leu Ser Pro
            515                 520                 525

Gly Gly Leu Leu Ala Asp Thr Trp Ala His Gln Glu Gly Thr His Pro
        530                 535                 540

Arg Asp Arg Asn Val Glu Lys Leu Gln Val Leu Leu Asn Cys Ile Thr
545                 550                 555                 560

Glu Ile Tyr Tyr Gln Phe Lys Lys Asp Lys Ala Glu Arg Arg Leu Ala
            565                 570                 575

Tyr Asn Glu Glu Gln Ile His Lys Phe Asp Lys Gln Lys Leu Tyr Tyr
            580                 585                 590

His Ala Thr Lys Ala Met Ser His Phe Ser Glu Glu Cys Val Arg Lys
            595                 600                 605

Tyr Glu Ala Phe Lys Asp Lys Ser Glu Glu Trp Met Arg Lys Met Leu
            610                 615                 620

His Leu Arg Lys Gln Leu Leu Ser Leu Thr Asn Gln Cys Phe Asp Ile
625                 630                 635                 640

Glu Glu Glu Val Ser Lys Tyr Gln Asp Tyr Thr Asn Glu Leu Gln Glu
            645                 650                 655

Thr Leu Pro Gln Lys Met Leu Ala Ala Ser Gly Gly Val Lys His Ala
            660                 665                 670

Met Ala Pro Ile Tyr Pro Ser Ser Asn Thr Leu Val Glu Met Thr Leu
            675                 680                 685

Gly Met Lys Lys Leu Lys Glu Glu Met Glu Gly Val Val Lys Glu Leu
            690                 695                 700

Ala Glu Asn Asn His Ile Leu Glu Arg Phe Gly Ser Leu Thr Met Asp
705                 710                 715                 720

Gly Gly Leu Arg Asn Val Asp Cys Leu
            725
```

NUCLEIC ACIDS ENCODING IKR-2, A PROTEIN KINASE RELATED TO THE I KAPPA B KINASES

CROSS-REFERENCE TO RELATED APPLICATION

This application is a national application under 35 U.S.C. §371 of International Application No. PCT/US99/17578, having an international filing date of Aug. 4, 1999 and published in English on Feb. 17, 2000; which claims the benefit under 35 U.S.C. §119(e) of U.S. provisional application No. 60/118,783, filed Feb. 5, 1999, and of U.S. provisional application No. 60/099,973, filed Sep. 11, 1998, and of U.S. provisional application No. 60/095,269, filed Aug. 4, 1998. Each of these applications is incorporated herein by reference in its entirety.

BACKGROUND OF THE INVENTION

1. Field of the Invention

The invention is directed to purified and isolated novel I kappa B kinase-related kinases 1 and 2 (IKR-1 and IKR-2) polypeptides and fragments thereof, the nucleic acids encoding such polypeptides, processes for production of recombinant forms of such polypeptides, antibodies generated against these polypeptides, fragmented peptides derived from these polypeptides, and uses thereof.

2. Description of Related Art

The transcription factor NF-κB (nuclear factor κB) is composed of homo- or heterodimers of proteins from the Rel family of transcription factors. The major genes regulated by NF-κB are immune, viral, and inflammatory response genes (C. H. Regnier et al., *Cell, Vol.* 90: 373–383, July 1997). When NF-κB is not involved in active transcription of these genes, it is located in the cytoplasm bound to the inhibitory protein IκB which regulates the activity of NF-κB (J. A. DiDonato et al., *Nature,* Vol. 388: 548–554, August 1997). IκB, when bound to NF-κB molecules, masks the nuclear localization signal of NF-κB, thus inactivating the protein.

In response to extracellular cytokines or other proinflammatory stimuli, IκB molecules are quickly phosphorylated by intracellular kinases such as I Kappa B kinases α and β (IKKα and IKKβ). Once activated, IKKα and IKKβ specifically phosphorylate IκB at specific serine residues in the N-terminus or IκB alpha at serine residues 32 and 36, thereby targeting this molecule for proteolytic destruction. The outcome of IκB phosphorylation and destruction is the release and subsequent translocation of NF-κB from the cytosol to the nucleus where it engages transcriptional regulatory sites on a number of immune related and proinflammatory genes.

The eukaryotic protein kinases make up a large and rapidly expanding family of proteins related on the basis of homologous catalytic domains. Spurred by the development of gene cloning and sequencing methodologies, distinct protein kinase genes have been identified from a wide selection of invertebrates and lower eukaryotes, including *Drosophila, Caenorhabditis elegans, Aplysia, Hydra, Dictyostelium,* and budding (*Saccharomyces cerevisiae*) and fission (*Schizosaccharomyces pombe*) yeast. Homologous genes have also been identified in higher plants. Protein kinases, however, are not limited to the eukaryotes. Enzyme activities have been well documented in prokaryotes, but the prokaryotic protein kinase genes are not obviously homologous to those of the eukaryotes.

Given the important function of kinases in general and IKK's specifically, there is a need in the art for additional members of the kinase family. In addition, in view of the continuing interest in protein research, the discovery, identification, and roles of new proteins, such as protein kinases, are at the forefront of modern molecular biology and biochemistry. Despite the growing body of knowledge, there is still a need in the art for the identity and function of proteins having kinase activities. In addition, because there is an unmet need for therapeutic compounds which interfere with activation of NF-κB and because protein kinases are useful biochemical reagents, there is also need in the art for the continued discovery of unique members of the IKB protein kinase family and potential therapeutic targets thereof.

In another aspect, the identification of the primary structure, or sequence, of an unknown protein is the culmination of an arduous process of experimentation. In order to identify an unknown protein, the investigator can rely upon a comparison of the unknown protein to known peptides using a variety of techniques known to those skilled in the art. For instance, proteins are routinely analyzed using techniques such as electrophoresis, sedimentation, chromatography, sequencing and mass spectrometry.

In particular, comparison of an unknown protein to polypeptides of known molecular weight allows a determination of the apparent molecular weight of the unknown protein (T. D. Brock and M. T. Madigan, *Biology of Microorganisms* 76–77 (Prentice Hall, 6d ed. 1991)). Protein molecular weight standards are commercially available to assist in the estimation of molecular weights of unknown protein (New England Biolabs Inc. Catalog:130–131, 1995; J. L. Hartley, U.S. Pat. No. 5,449,758). However, the molecular weight standards may not correspond closely enough in size to the unknown protein to allow an accurate estimation of apparent molecular weight. The difficulty in estimation of molecular weight is compounded in the case of proteins that are subjected to fragmentation by chemical or enzymatic means, modified by post-translational modification or processing, and/or associated with other proteins in non-covalent complexes.

In addition, the unique nature of the composition of a protein with regard to its specific amino acid constituents results in unique positioning of cleavage sites within the protein. Specific fragmentation of a protein by chemical or enzymatic cleavage results in a unique "peptide fingerprint" (D. W. Cleveland et al., *J. Biol. Chem.* 252:1102–1106, 1977; M. Brown et al., *J. Gen. Virol.* 50:309–316, 1980). Consequently, cleavage at specific sites results in reproducible fragmentation of a given protein into peptides of precise molecular weights. Furthermore, these peptides possess unique charge characteristics that determine the isoelectric pH of the peptide. These unique characteristics can be exploited using a variety of electrophoretic and other techniques (T. D. Brock and M. T. Madigan, *Biology of Microorganisms* 76–77 (Prentice Hall, 6d ed. 1991)).

Fragmentation of proteins is further employed for amino acid composition analysis and protein sequencing (P. Matsudiara, *J. Biol. Chem.* 262:10035–10038, 1987; C. Eckerskorn et al., *Electrophoresis* 1988, 9:830–838, 1988), particularly the production of fragments from proteins with a "blocked" N-terminus. In addition, fragmented proteins can be used for immunization, for affinity selection (R. A. Brown, U.S. Pat. No. 5,151,412), for determination of modification sites (e.g. phosphorylation), for generation of active biological compounds (T. D. Brock and M. T. Madigan, *Biology of Microorganisms* 300–301 (Prentice Hall, 6d ed. 1991)), and for differentiation of homologous proteins (M. Brown et al., *J. Gen. Virol.* 50:309–316, 1980).

In addition, when a peptide fingerprint of an unknown protein is obtained, it can be compared to a database of known proteins to assist in the identification of the unknown protein using mass spectrometry (W. J. Henzel et al., *Proc. Natl. Acad. Sci. USA* 90:5011–5015, 1993; D. Fenyo et al., *Electrophoresis* 19:998–1005, 1998). A variety of computer software programs to facilitate these comparisons are accessible via the Internet, such as Protein Prospector (prospector.uscf.edu), MultiIdent (expasy.ch/sprot/multiident.html), PeptideSearch (mann.embl-heiedelberg.de/deSearch/FR_PeptideSearchForm.html), and ProFound (chait-sgi.rockefeller.edu/cgi-bin/prot-id-frag.html). These programs allow the user to specify the cleavage agent and the molecular weights of the fragmented peptides within a designated tolerance. The programs compare these molecular weights to protein molecular weight information stored in databases to assist in determining the identity of the unknown protein. Accurate information concerning the number of fragmented peptides and the precise molecular weight of those peptides is required for accurate identification. Therefore, increasing the accuracy in determining the number of fragmented peptides and their molecular weight should result in enhanced likelihood of success in the identification of unknown proteins.

In addition, peptide digests of unknown proteins can be sequenced using tandem mass spectrometry (MS/MS) and the resulting sequence searched against databases (J. K. Eng, et al., *J. Am. Soc. Mass Spec.* 5:976–989 (1994); M. Mann and M. Wilm, *Anal. Chem.* 66:4390–4399 (1994); J. A. Taylor and R. S. Johnson, *Rapid Comm. Mass Spec.* 11: 1067–1075 (1997)). Searching programs that can be used in this process exist on the Internet, such as Lutefisk 97 (Isbc.com:70/Lutefisk97.html), and the Protein Prospector, Peptide Search and ProFound programs described above. Therefore, adding the sequence of a gene and its predicted protein sequence and peptide fragments to a sequence database can aid in the identification of unknown proteins using tandem mass spectrometry.

Thus, there also exists a need in the art for polypeptides suitable for use in peptide fragmentation studies, for use in molecular weight measurements, and for use in protein sequencing using tandem mass spectrometry.

SUMMARY OF THE INVENTION

The invention aids in fulfilling these various needs in the art by providing isolated IKR-1 and IKR-2 nucleic acids and polypeptides encoded by these nucleic acids. Particular embodiments of the invention are directed to isolated IKR nucleic acid molecules (IKR-1 and IKR-2) comprising the DNA sequence of SEQ ID NOs:1 and 3 and isolated IKR nucleic acid molecules encoding the amino acid sequences of SEQ ID NOs:2 and 4, as well as nucleic acid molecules complementary to these sequences. The invention also encompasses recombinant vectors that direct the expression of the nucleic acid molecules of the invention and host cells stably or transiently transformed or transfected with these vectors.

In addition, the invention encompasses methods of using the nucleic acids noted above to identify nucleic acids encoding proteins having kinase function and to study cell signal transduction and activation of transcription factors such as the NF-κB family of molecules.

The invention also encompasses isolated polypeptides and fragments thereof encoded by these nucleic acid molecules. The invention further encompasses methods for the production of these polypeptides, including culturing a host cell under conditions promoting expression and recovering the polypeptide from the culture medium. Especially, the expression of these polypeptides in bacteria, yeast, plant, insect, and animal cells is encompassed by the invention.

In general, the polypeptides of the invention can be used to study cellular processes such as immune regulation, cell proliferation, cell death, cell migration, cell-to-cell interaction, inflammatory responses, and cell signal transduction. In addition, these polypeptides can be used to identify proteins associated with IKR kinases.

In addition, the invention includes assays utilizing these polypeptides to screen for potential inhibitors of their kinase activity and methods of using these polypeptides as therapeutic agents for the treatment of diseases mediated by IKR polypeptide counter-structure molecules (including substrates, regulatory proteins, small molecules, etc.). Further, methods of using these polypeptides in the design of inhibitors thereof are also an aspect of the invention.

The invention further provides a method for using these polypeptides as molecular weight markers that allow the estimation of the molecular weight of a protein or a fragmented protein, as well as a method for the visualization of the molecular weight markers of the invention thereof using electrophoresis. The invention further encompasses methods for using the polypeptides of the invention as markers for determining the isoelectric point of an unknown protein, as well as controls for establishing the extent of fragmentation of a protein.

Further encompassed by this invention are kits to aid in these determinations.

Further encompassed by this invention is the use of the IKR nucleic acid sequences, predicted amino acid sequences of the polypeptide or fragments thereof, or a combination of the predicted amino acid sequences of the polypeptide and fragments thereof for use in searching an electronic database to aid in the identification of sample nucleic acids and/or proteins.

Isolated polyclonal or monoclonal antibodies that bind to these polypeptides are also encompassed by the invention, as well as the use of these antibodies to aid in purifying IKR polypeptides.

BRIEF DESCRIPTION OF THE FIGURES

This invention will be more fully described with reference to the drawings in which:

FIG. 1 is the nucleotide sequence of IKR-1 SEQ ID NO:1;

FIG. 2 is the nucleotide sequence of IKR-2 SEQ ID NO:3;

FIG. 3 is the amino acid sequence of IKR-1 SEQ ID NO:2; and

FIG. 4 is the amino acid sequence of IKR-2 SEQ ID NO:4.

DETAILED DESCRIPTION OF THE INVENTION

The nucleic acid molecules encompassed in the invention include the following nucleotide sequences:

NAME:IKR-1

Nucleotide sequence:

1 CACAGGAAAC AGCTATGACC ATGATTACGC CAAGCTCGAA ATTAACCCTC

51 ACTAAAGGGA ACAAAAGCTG GAGCTCCACC GCGGTGGCGG CCGCTCTAGA

101 ACTAGTGGAT CCCCCGGGCT GCAGGAATTC CGGCCTGGGA CTGGGTACCC

151 CACTGCTCTC AGAGAGGCAG GAAAGAGACC TTCAGGCTCA AGACCATCAC
201 CTGCTTTGCC TGTGGATCCT GGGGGGCCCC ATAGCTACCA GGATCTTCTA
251 GGCACTGCCC AGGATTGACT TCAAGGCCTG AATCCCTGGG GGTGCCACCC
301 AGTTCCACAA GTCTGCATTG CCCTGCAACT GAGATAGGAG ATGGGGAAGA
351 AGATAGCCAA GCCCAGGAGA TGCAGAGTAC CACTAACTAC CTGTGGCATA
401 CTGATGACCT GCTAGGGCAG GGGGCCACTG CCAGTGTGTA CAAGGCCCGA
451 AACAAGAAAT CCGGGGAGGT GGTTGCTGTA AAGGTCTTCA ACTCAGCCAG
501 CTATCGGCGA CCTCCTGAGG TTCAGGTGAG GGAGTTTGAG GTCCTGCGGA
551 GGCTGAATCA CCAGAACATC GTGAAGCTAT TCGCAGTGGA GGAAACGGGA
601 GGCAGCCGGC AGAAGGTGCT AATCATGGAG TACTGCTCCA GTGGGAGCCT
651 GCTGAGCGTG CTGGAAGACC CTGAGAACAC GTTCGGGCTT TCTGAAGAGG
701 AGTTCCTAGT GGTGCTGCGC TGTGTGGTGG CTGGCATGAA CCACCTGCGG
751 GAGAATGGCA TTGTCCATCG GGACATCAAA CCTGGGAACA TCATGCGCCT
801 GGTGGGCGAG GAGGGGCAGA GCATCTATAA GCTGTCTGAC TTCGGGGCTG
851 CCCGCAAGCT GGACGATGAT GAGAAGTTTG TTTCTGTCTA TGGTACAGAG
901 GAATACCTGC ACCCTGACAT GTATGAGCGT GCAGTGCTGC GCAAACCCCA
951 GCAAAAGGCA TTTGGTGTGA CTGTGGATCT CTGGAGTATT GGGGTGACCC
1001 TGTACCACGC AGCCACAGGC AGTCTGCCCT TCATCCCCTT CGGTGGGCCC
1051 CGGCGCAACA AAGAGATCAT GTACAGAATC ACCACAGAGA AGCCAGCCGG
1101 GGCCATTTCA GGGACTCAGA AGCACGAAAA TGGTCCCTTG GAGTGGAGCT
1151 ACAGCCTCCC CATCACCTGT AGACTGTCCA TGGGACTGCA GAACCAGCTG
1201 GTGCCCATCC TGGCCAACAT CCTGGAGGTG GAAGAGGATA AGTGCTGGGG
1251 CTTTGATCAG TTCTTCGCGG AGACCAGTGA CATTCTGCAG CGAACGGTCA
1301 TCCACGTCTT TTCCCTACCC CAGGCCGTTT TGCATCATGT CTACATCCAC
1351 GCCCACAACA CGATTGCCAT CTTTTTGGAG GCTGTATATG AGCAGACCAA
1401 CGTGACCCCC AAACACCAGG AGTACCTCTT CGAGGGTCAC CCTTGTGTCC
1451 TTGAGCCAAG CCTCTCAGCC CAGCACATCG CCCACACAGC TGCCAGCAGC
1501 CCTCTAACTC TGTTCAGCAT GTCCAGCGAC ACACCTAAGG GGCTGGCCTT
1551 CAGGGACCCT GCTCTGGATG TCCCAAAGTT CGTCCCTAAG GTTGACCTAC
1601 AGGCCGATTA CAGCAGGCT AAGGGGGTGC TGGGCGCTGG CTACCAGGCC
1651 CTGTGGCTGG CGCGGGTCCT GCTGGATGGA CAGGCGTTGA TGCTTCGGGG
1701 GTTACATTGG GTCCTGGAGG TGCTTCAGGA CACGTGCCAG CAGACACTGG
1751 AGGTCACACG GACAGCCCTC CTCTACCTCA GCAGCAGCCT GGGCACTGAA
1801 AGGTTCAGCA GTGGAGCGGG GATGCCTGAC GTCCAGGAAC GAAAGGAGGC

1851 CACAGAGCTA AGAACCAGGC TGCAGACTCT CTCAGAGATC CTGTCTAAAT
1901 GTTCCCACAA TGTCACAGAA ACCCAAAGGA GCCTGAGCTG TCTGGGTGAA
1951 GAGCTTTTAA AGAACCGGGA CCAGATTCAT GAGGATAACA AAAGTATCCA
2001 GAAGATTCAG TGTTGTTTGG ACAAGATGCA CTTCATCTAC AAACAGTTCA
2051 AGAAATCCAG GATGAGGCCA GGGCTCAGCT ACAATGAGGA GCAGATCCAC
2101 AAGCTGGATA AGGTAAATTT CAGTCATCTA GCCAAGAGGC TGCTGCAGGT
2151 GTTCCAGGAG GAGTGTGTGC AGACGTATCA GGTGTCGCTG GTCACACACG
2201 GCAAGCGGAT GAGGCAGGTG CAGAGGGCCC AGAACCACCT GCATCTCATT
2251 GGCCACTCTG TGGCCACCTG TAACTCGGAA GCCCGGGGAG CCCAGGAGAG
2301 TCTGAACAAG ATCTTTGATC AGCTCCTTCT GGACAGACT TCCGAACAGG
2351 GAGCTGAGGT GTCACCGCAA CCTATGGCTC CTCATCCCGG CCCTGATCCG
2401 AAGGACCTGG TCTTCCACAT GCAGGAGCTT TGTAATGATA TGAAGCTATT
2451 GGCCTTTGAT CTCCAGGACA CAACCGACT CATCGAACGG TTACATAGAG
2501 TTCCATCGGC ACCAGATGTC TGAGCTCCCT GGGGGTTCAC AAGGCACTCA
2551 GAAGCAATAG AAACATTCAT ATTGTACCCC TACACTGTGA GACCAAATTC
2601 AGGGCAAGTT CTGGTTCCAT CTCACTAGCC TACCTCCCTC TTGGCCATTG
2651 GCCATTGGCC AACAAACTAG CATTACTTTG ACTGTCCTCT TGGGAAGCAG
2701 CTAGGACAGG GACTCCTGGC CATCCCAGGC AGTATCTACA GAAGAGACCA
2751 TGCGGCTACC ACAGCCTTAT CAAGACACCA AGACTGTTCT TCCTCACCCA
2801 GGCTCTGGAG GTCTGGTCTT GGAAAGAAAA GGCTCAGCCC TCTCACGCTC
2851 TGCACTTCCC AGGACCAGCA GGCGTCTCCT GTGGCTTCTC CTGCCTCTCC
2901 AGGGTGCTGG ATCAGAATGC TTATTCTTGG TTGTTTCCTG TGCTGCTTCC
2951 TGAGTGTCCC CATCCCTGGC CTCAGGCAAC CCACAAACGG CCCCTCTGTG
3001 CTTGGTCTAG ATGCACCTGC ATTTGAGAAA GTGGGTGGTT GAGGCTAACT
3051 GCTGGTGCTT TGAGGATTCT CCTTGACCTT TTCTCCGAGG AACGCTTGGT
3101 TCTAAGAAAC AGCTGGTCAG TATCAACCAC AGCCATGCTA ACTGGACAGA
3151 TGTTGGAACC CAAAGTCCTA AGGAGAGAGC AGGCCTGCAC CTTCAGACAT
3201 GGAATAAATA CATCGCCTTT TCTGTTTAAA AAAAAAAAAA AAAAACCGGA
3251 ATTCGATATC AAGCTTATCG ATACCGTCGA CCTCGAGGGG GGGCCCGGTA
3301 CCCAATTCGC CCTATAGTGA GTCGTATTAC AATTCACTGG CCGTCGTTTT
3351 ACAACGTCGT GACTGGGAAA ACCCTGGCGT TACCC (SEQ ID NO:1)

NAME:IKR-2
Nucleotide sequence:
1 TTGGGTAACG CCAGGGTTTT CCCAGTCACG ACGTTGTAAA ACGACGGCCA
51 GTGAATTGTA ATACGACTCA CTATAGGGCG AAT-TGGGTAC CGGGCCCCCC 101 CTCGAGGTCG ACGGTATCGA TAAGCTTGAT ATCGAATTCC GGCACTCGCG
151 GGCATACATG CAAATCTCTT CTTCCCCCTT ATCGTGAGGA GAAGCGCCTG
201 GACAAGCCGA GATGCAGAGC ACCTCCAACC ATCTGTGGCT CCTGTCTGAT
251 ATCCTAGGCC AGGGGGCCAC TGCAAATGTC TTCCGAGGAA GGCATAAGAA
301 AACTGGTGAT CTCTATGCTG TCAAAGTATT TAATAACATA AGCTTCCTTC
351 GCCCAGTGGA TGTTCAAATG AGAGAATTTG AAGTGTTAAA AAAACTCAAT
401 CACAAAAACA TTGTCAAGTT ATTTGCTATT GAAGAGGAGA CAACAACAAG
451 ACATAAAGTG CTTATTATGG AGTTTTGTCC CTGTGGGAGT TTATACACTG
501 TTCTAGAGGA GCCGTCCAAT GCGTATGGAC TTCCAGAATC AGAATTTCTC
551 ATTGTCTTAC GAGATGTGGT GGGCGGGATG AATCATCTCC GAGAGAACGG
601 CATAGTGCAC CGAGATATCA AGCCAGGCAA CATCATGCGC GTCATAGGGG
651 AGGACGGCCA GTCTGTGTAC AAACTCACGG ATTTCGGCGC CGCTCGAGAG
701 CTGGAGGACG ATGAGCAGTT TGTGTCTCTG TACGGCACAG AAGAGTACCT
751 GCATCCGGAC ATGTATGAAA GGGCAGTGCT AAGAAAGGAC CATCAGAAGA
801 AGTACGGGGC TACCGTTGAT CTGTGGAGTG TTGGAGTGAC ATTCTACCAT
851 GCAGCCACGG GGTCGCTGCC GTTTAGACCC TTCGAGGGGC CTCGGAGGAA
901 CAAAGAAGTA ATGTATAAAA TAATCACTGG GAAGCCGTCT GGTGCAATAT
951 CTGGAGTACA GAAAGCAGAA AACGGACCAA TTGACTGGAG TGGAGACATG
1001 CCTCTCTCCT GTAGTCTTTC TCAGGGTCTT CAGGCACTGC TTACCCCAGT
1051 TCTTGCAAAC ATACTTGAAG CTGATCAGGA GAAGTGCTGG GGTTTTGACC
1101 AGTTCTTTGC AGAGACCAGT GATGTGCTTC ACCGAATGGT GATCCATGTC
1151 TTCTCGCTAC AACACATGAC GGCGCATAAG ATTTACATTC ACAGCTATAA
1201 CACTGCTGCT GTGTTCCATG AACTGGTCTA TAAACAAACC AAGATTGTTT
1251 CCTCAAATCA AGAACTTATC TACGAAGGAC GACGCTTAGT CCTAGAACTC
1301 GGACGACTAG CCCAGCATTT TCCTAAAACC ACAGAGGAAA ATCCTATCTT
1351 TGTCACGAGC CGGGAACAAC TCAATACCGT AGGACTGAGA TATGAAAAAA
1401 TTTCCCTCCC TAAAATACAT CCACGCTATG ATCTGGATGG GGACGCCAGC
1451 ATGGCCAAGG CAGTGACGGG GGTTGTGTGC TACGCCTGCA GAACTGCCAG
1501 TACCCTGCTG CTCTATCAAG AATTAATGCG AAAGGGGGTA CGGTGGCTGG
1551 TTGAACTGGT TAAGGATGAT TACAACGAGA CCGTCCACAA GAAGACGGAG
1601 GTAGTGATCA CACTGGATTT CTGCATCAGG AACATTGAGA AGACTGTGAA
1651 AGTGTATGAG AAGTTGATGA AGGTCAACCT GGAAGCCGCA GAGCTGGGTG
1701 AGATTTCAGA CATACACACC AAGCTGCTGA GACTTTCCAG TTCTCAGGGA
1751 ACAATAGAAA GCAGTCTTCA GGACATCAGC AGCAGGCTGT CTCCAGGGGG
1801 CTTGCTGGCC GACACCTGGG CACATCAAGA AGGCACGCAT CCAAGAGACA
1851 GGAATGTAGA AAAACTGCAG GTCCTGTTGA ACTGCATCAC AGAGATTTAC
1901 TATCAGTTCA AAAAAGACAA AGCAGAACGC AGACTAGCTT ATAATGAAGA
1951 ACAGATCCAC AAATTTGATA AGCAAAAATT GTATTACCAT GCCACAAAAG
2001 CAATGAGCCA CTTCTCAGAA GAATGTGTTA GAAAGTATGA AGCGTTTAAA
2051 GATAAGTCGG AAGAGTGGAT GAGAAAGATG CTTCATCTTA GGAAGCAGCT
2101 GTTATCGCTA ACTAATCAGT GTTTCGATAT CGAAGAGGAA GTGTCCAAGT
2151 ATCAAGACTA TACTAACGAG TTACAAGAAA CTCTGCCTCA GAAAATGCTC
2201 GCAGCCTCCG GCGGCGTCAA GCACGCCATG GCCCCGATCT ACCCCAGCTC
2251 TAACACCTTA GTGGAGATGA CTCTTGGTAT GAAGAAGTTA AAGGAGGAGA
2301 TGGAAGGCGT GGTTAAGGAG CTGGCCGAGA ACAATCATAT TTTAGAAAGG
2351 TTTGGGTCTT TAACAATGGA TGGTGGCCTT CGCAATGTGG ACTGTCTTTA
2401 GCTTCCTAGG GAGTCTGGGA AGTTCTAGTT TGCACAAGAA GATAACACTG
2451 GGGCACGAAA TGAACACCTT TGTGAATGGA GTTCTTATTT CTACACTTCA
2501 GTATTTGATG AGGTCATGTA AATATGTACA GTTTGTAAAT ACATATACAT
2551 ATATATATAT ATATATGAAT TTTGGCTGCT GTAACAAAGA CAGATTGACC
2601 TCAGCGAGCT GTAGAAGAAA GCCATGACCA GCCAGTGCTT TGGGGTGCTC
2651 TCCCTAATTC TTCACATAAG CTGGAGAAAA TCAATTGCTT GGTGCCTAAA
2701 GAAAGTATTT TTTGAATTGG CATTCTTAAA ATTTTGAAAG GACTGATAGT
2751 CGACACAGTG TAACTGGAGG AGACACAGGG CTTTGTGACG GGAACAGAAC
2801 CGCGGTTTAA CCACAGTCGG TTCCCTGACA AGGATAAAGT GGCATTATCT
2851 CATTTGACCG GGTGCCCAAA TCTCAGTTTT CCTCGGATGT TTGATTTTAG
2901 GTGAATTATT GAGCAAAAAC TTTAAAGTGA ATTCATTGTT TAAACTATTC
2951 ATTTTTCCTT TGGTCATGAA TGTGTAATTG TCATTCAGAT CCTAGTATCA
3001 TTTCAATTGT CTTAAGATGT ATATTTCTGT ACTTTAATTC TGCTATTTCA
3051 TGAAAAAATA AATTTCTCCC GGAATTCCTG CAGCCCGGGG GATCCACTAG
3101 TTCTAGAGCG GCCGCCACCG CGGTGGAGCT CCAGCTTTTG TTCCCTTTAG
3151 TGAGGGTTAA TTTCGAGCTT GGCGTAATCA TGGTCATAGC TGTTTCCTGT
3201 GTGAAATTGT TATCCGCTC (SEQ ID NO:3)

The amino acid sequences of the polypeptides encoded by the nucleotide sequence of the invention include:

Name IKR-1 (Polypeptide)

1 MQSTTNYLWH TDDLLGQGAT ASVYKARNKK SGEVVAVKVF NSASYRRPPE
51 VQVREFEVLR RLNHQNIVKL FAVEETGGSR QKVLIMEYCS SGSLLSVLED
101 PENTFGLSEE EFLVVLRCVV AGMNHLRENG IVHRDIKPGN IMRLVGEEGQ
151 SIYKLSDFGA ARKLDDDEKF VSVYGTEEYL HPDMYERAVL RKPQQKAFGV

201 TVDLWSIGVT LYHAATGSLP FIPFGGPRRN KEIMYRITTE KPAGAISGTQ
251 KHENGPLEWS YSLPITCRLS MGLQNQLVPI LANILEVEED KCWGFDQFFA
301 ETSDILQRTV IHVFSLPQAV LHHVYIHAHN TIAIFLEAVY EQTNVTPKHQ
351 EYLFEGHPCV LEPSLSAQHI AHTAASSPLT LFSMSSDTPK GLAFRDPALD
401 VPKFVPKVDL QADYSTAKGV LGAGYQALWL ARVLLDGQAL MLRGLHWVLE
451 VLQDTCQQTL EVTRTALLYL SSSLGTERFS SGAGMPDVQE RKEATELRTR
501 LQTLSEILSK CSHNVTETQR SLSCLGEELL KNRDQIHEDN KSIQKIQCCL
551 DKMHFIYKQF KKSRMRPGLS YNEEQIHKLD KVNFSHLAKR LLQVFQEECV
601 QTYQVSLVTH GKRMRQVQRA QNHLHLIGHS VATCNSEARG AQESLNKIFD
651 QLLLDRASEQ GAEVSPQPMA PHPGPDPKDL VFHMQELCND MKLLAFDLQD
701 NNRLIERLHR VPSAPDV (SEQ ID NO:2)

Name:IKR-2 (Polypeptide)
1 MQSTSNHLWL LSDILGQGAT ANVFRGRHKK TGDLYAVKVF NNISFLRPVD
51 VQMREFEVLK KLNHKNIVKL FAIEEETTTR HKVLIMEFCP CGSLYTVLEE
101 PSNAYGLPES EFLIVLRDVV GGMNHLRENG IVHRDIKPGN IMRVIGEDGQ
151 SVYKLTDFGA ARELEDDEQF VSLYGTEEYL HPDMYERAVL RKDHQKKYGA
201 TVDLWSVGVT FYHAATGSLP FRPFEGPRRN KEVMYKIITG KPSGAISGVQ
251 KAENGPIDWS GDMPLSCSLS QGLQALLTPV LANILEADQE KCWGFDQFFA
301 ETSDVLHRMV IHVFSLQHMT AHKIYIHSYN TAAVFHELVY KQTKIVSSNQ
351 ELIYEGRRLV LELGRLAQHF PKTTEENPIF VTSREQLNTV GLRYEKISLP
401 KIHPRYDLDG DASMAKAVTG VVCYACRTAS TLLLYQELMR KGVRWLVELV
451 KDDYNETVHK KTEVVITLDF CIRNIEKTVK VYEKLMKVNL EAAELGEISD
501 IHTKLLRLSS SQGTIESSLQ DISSRLSPGG LLADTWAHQE GTHPRDRNVE
551 KLQVLLNCIT EIYYQFKKDK AERRLAYNEE QIHKFDKQKL YYHATKAMSH
601 FSEECVRKYE AFKDKSEEWM RKMLHLRKQL LSLTNQCFDI EEEVSKYQDY
651 TNELQETLPQ KMLAASGGVK HAMAPIYPSS NTLVEMTLGM KKLKEEMEGV
701 VKELAENNHI LERFGSLTMD GGLRNVDCL (SEQ ID NO: 4)

The discovery of the nucleic acids of the invention enables the construction of expression vectors comprising nucleic acid sequences encoding polypeptides; host cells transfected or transformed with the expression vectors; isolated and purified biologically active polypeptides and fragments thereof. The invention also enables the use of the nucleic acids or oligonucleotides thereof as probes to identify nucleic acid encoding proteins having kinase function. The discovery further provides for the use of such polypeptides and soluble fragments to function as a kinase. The polypeptides and fragments can also generate antibodies, and among the uses of such antibodies is the purification of IKR polypeptides. Finally, the invention enables the use of such polypeptides and fragmented peptides as molecular weight markers and as controls for peptide fragmentation, as well as kits comprising these reagents.

Nucleic Acid Molecules

In a particular embodiment, the invention relates to certain isolated nucleotide sequences that are free from contaminating endogenous material. A "nucleotide sequence" refers to a polynucleotide molecule in the form of a separate fragment or as a component of a larger nucleic acid construct. The nucleic acid molecule has been derived from DNA or RNA isolated at least once in substantially pure form and in a quantity or concentration enabling identification, manipulation, and recovery of its component nucleotide sequences by standard biochemical methods (such as those outlined in Sambrook et al., *Molecular Cloning: A Laboratory Manual,* 2nd sed., Cold Spring Harbor Laboratory, Cold Spring Harbor, N.Y. (1989)). Such sequences are preferably provided and/or constructed in the form of an open reading frame uninterrupted by internal non-translated sequences, or introns, that are typically present in eukaryotic genes. Sequences of non-translated DNA can be present 5' or 3' from an open reading frame, where the same do not interfere with manipulation or expression of the coding region.

Nucleic acid molecules of the invention include DNA in both single-stranded and double-stranded form, as well as the RNA complement thereof. DNA includes, for example, cDNA, genomic DNA, chemically synthesized DNA, DNA amplified by PCR, and combinations thereof Genomic DNA may be isolated by conventional techniques, e.g., using the cDNA of SEQ ID NOs:1 and 2, or a suitable fragment thereof, as a probe.

The DNA molecules of the invention include full length genes as well as polynucleotides and fragments thereof. Other embodiments include DNA encoding a truncated version of the kinase containing, for example, only the kinase catalytic domain or a catalytically inactive mutant thereof.

Preferred Sequences

Particularly preferred nucleotide sequences of the invention are SEQ ID NOs:1 and 3, as set forth above. cDNA clones having the nucleotide sequence of SEQ ID NOs:1 and 3 were isolated as described in Example 1. Briefly, a mouse transit amplifying (TRAM) cell EST library was queried using the tBlastN algorithm to identify sequences related to KIAA 0151 (GenBank accession number D63485), a kinase of unknown function which appears to be closely related to the I kappa B kinase (IKK) family of kinases. Query results yielded IKR-1 and IKR-2 ESTs which were then used to isolate IKR-1 and IKR-2 cDNA clones from the murine T-cell line bacteriophage library EL46.1N7ZAP.

IKR-1 and IKR-2 share 46% identity (56% similarity) to one another, whereas IKR-1 has 83% identity (87% similarity) with KIAA0151 and IKR-2 has 49% identity (58% similarity) with KIAA 0151. Homologies of IKR-1 and IKR-2 toward the IKK family members are not as high as homologies to KIAA 0151, generally in the range of 20% identiiy and 30% similarity. IKR-2 also exhibits 94% identity to a recent entry (W60724) in the Derwent Geneseq database which describes a new protein kinase T2K that specifically phosphorylates IkappaB.

The sequences of amino acids encoded by the DNA of SEQ ID NOs:1 and 3 are shown in SEQ ID NOs:2 and 4. These sequences identify the IKR polynucleotides as members of the I kappa B kinase-related family. Members of this family such as IKKα and IKKβ are activated in response to cytokine or other pro-inflammatory stimuli. Activated IKKα and IKKβ specifically phosphorylate the inhibitory subunit I kappa B (IκB) alpha, which is bound to the transcription factor NF-κB, at serine residues 32 and 36, thereby targeting this molecule for proteolytic destruction. Phosphorylation and destruction of IκB results in the release of NF-κB and its translocation from the cytosol to the nucleus where it engages transcriptional regulatory sites on a number of pro-inflammatory genes. The close similarity of the catalytic domains of IKR-1 and IKR-2 to the IKKs strongly suggest that they too will participate in the phosphorylation of IκB (or related molecules) and lead to the activation of NF-κB (or related transcription factors).

Additional Sequences

Due to the known degeneracy of the genetic code, wherein more than one codon can encode the same amino acid, a DNA sequence can vary from that shown in SEQ ID NOs:1 and 3, and still encode a polypeptide having the amino acid sequence of SEQ ID NOs:2 and 4. Such variant DNA sequences can result from silent mutations (e.g., occurring during PCR amplification), or can be the product of deliberate mutagenesis of a native sequence.

The invention thus provides isolated DNA sequences encoding polypeptides of the invention, selected from: (a) DNA comprising the nucleotide sequence of SEQ ID NOs:1 and 3; (b) DNA encoding the polypeptides of SEQ ID NOs:2 and 4; (c) DNA capable of hybridization to a DNA of (a) or (b) under conditions of moderate stringency and which encodes polypeptides of the invention; (d) DNA capable of hybridization to a DNA of (a) or (b) under conditions of high stringency and which encodes polypeptides of the invention, and (e) DNA which is degenerate as a result of the genetic code to a DNA defined in (a), (b), (c), or (d) and which encode polypeptides of the invention. Of course, polypeptides encoded by such DNA sequences are encompassed by the invention.

As used herein, conditions of moderate stringency can be readily determined by those having ordinary skill in the art based on, for example, the length of the DNA. The basic conditions are set forth by Sambrook et al. *Molecular Cloning: A Laboratory Manual,* 2 ed. Vol. 1, pp. 1.101–104, Cold Spring Harbor Laboratory Press, (1989), and include use of a prewashing solution for the nitrocellulose filters 5×SSC, 0.5% SDS, 1.0 mM EDTA (pH 8.0), hybridization conditions of about 50% formamide, 6×SSC at about 42° C. (or other similar hybridization solution, such as Stark's solution, in about 50% formamide at about 42° C.), and washing conditions of about 60° C., 0.5×SSC, 0.1% SDS. Conditions of high stringency can also be readily determined by the skilled artisan based on, for example, the length of the DNA. Generally, such conditions are defined as hybridization conditions as above, and with washing at approximately 68° C., 0.2×SSC, 0.1% SDS. The skilled artisan will recognize that the temperature and wash solution salt concentration can be adjusted as necessary according to factors such as the length of the probe.

In another embodiment, the nucleic acid molecules of the invention also comprise nucleotide sequences that are at least 80% identical to a native sequence. Also contemplated are embodiments in which a nucleic acid molecule comprises a sequence that is at least 90% identical, at least 95% identical, at least 98% identical, at least 99% identical, or at least 99.9% identical to a native sequence.

The percent identity may be determined by visual inspection and mathematical calculation. Alternatively, the percent identity of two nucleic acid sequences can be determined by comparing sequence information using the GAP computer program, version 6.0 described by Devereux et al. (*Nucl. Acids Res.* 12:387, 1984) and available from the University of Wisconsin Genetics Computer Group (UWGCG). The preferred default parameters for the GAP program include: (1) a unary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, eds., *Atlas of Protein Sequence and Structure,* National Biomedical Research Foundation, pp. 353–358, 1979; (2) a penalty of 3.0 for each gap and an additional 0.10 penalty for each symbol in each gap; and (3) no penalty for end gaps. Other programs used by one skilled in the art of sequence comparison may also be used.

The invention also provides isolated nucleic acids useful in the production of polypeptides. Such polypeptides may be prepared by any of a number of conventional techniques. A DNA sequence encoding an IKR-1 or IKR-2 polypeptide or desired fragment thereof may be subcloned into an expression vector for production of the polypeptide or fragment. The DNA sequence advantageously is fused to a sequence encoding a suitable leader or signal peptide. Alternatively, the desired fragment may be chemically synthesized using known techniques. DNA fragments also may be produced by restriction endonuclease digestion of a full length cloned DNA sequence, and isolated by electrophoresis on agarose gels. If necessary, oligonucleotides that reconstruct the 5' or 3' terminus to a desired point may be ligated to a DNA fragment generated by restriction enzyme digestion. Such oligonucleotides may additionally contain a restriction endonuclease cleavage site upstream of the desired coding sequence, and position an initiation codon (ATG) at the N-terminus of the coding sequence.

The well-known polymerase chain reaction (PCR) procedure also may be employed to isolate and amplify a DNA sequence encoding a desired protein fragment. Oligonucleotides that define the desired termini of the DNA fragment are employed as 5' and 3' primers. The oligonucleotides may additionally contain recognition sites for restriction endonucleases, to facilitate insertion of the amplified DNA fragment into an expression vector. PCR techniques are described in Saiki et al., *Science* 239:487 (1988); Recombinant DNA Methodology, Wu et al., eds., Academic Press, Inc., San Diego (1989), pp. 189–196; and *PCR Protocols: A Guide to Methods and Applications,* Innis et al., eds., Academic Press, Inc. (1990).

Polypeptides and Fragments Thereof

The invention encompasses polypeptides and fragments thereof in various forms, including those that are naturally occurring or produced through various techniques such as procedures involving recombinant DNA technology. Such forms include, but are not limited to, derivatives, variants, and oligomers, as well as fusion proteins or fragments thereof Polypeptides and Fragments Thereof The polypeptides of the invention include full length proteins (amino acids 1 to 717 of SEQ ID NO:2 and amino acids 1 to 729 of SEQ ID NO:4) encoded by the nucleic acid sequences set forth above. Particularly preferred polypeptides comprise the amino acid sequence of SEQ ID NOs:2 and 4 with particularly preferred fragments comprising the N-terminal kinase domain (amino acids 1 to 300) of SEQ ID NOs:2 and 4.

The invention also provides polypeptides and fragments of the kinase domain that retain a desired biological activity. Particular embodiments are directed to polypeptide fragments that retain the ability to bind "binding partners", native cognates, substrates, or counter-structures. Such a fragment may be a soluble polypeptide. In another embodiment, the polypeptides and fragments advantageously include regions that are conserved in the I kappa B kinase family as described above.

Also provided herein are polypeptide fragments comprising at least 20, or at least 30, contiguous amino acids of the sequence of SEQ ID NOs:2 and 4. Fragments derived from different domains find use in studies of signal transduction and in regulating cellular processes associated with transduction of biological signals. Polypeptide fragments also may be employed as immunogens, in generating antibodies.

Variants

Naturally occurring variants as well as derived variants of the polypeptides and fragments are provided herein.

Variants may exhibit amino acid sequences that are at least 80% identical. Also contemplated are embodiments in which a polypeptide or fragment comprises an amino acid sequence that is at least 90% identical, at least 95% identical, at least 98% identical, at least 99% identical, or at least 99.9% identical to the preferred polypeptide or fragment thereof. Percent identity may be determined by visual inspection and mathematical calculation. Alternatively, the percent identity of two protein sequences can be determined by comparing sequence information using the GAP computer program, based on the algorithm of Needleman and Wunsch (J. Mol. Bio. 48:443, 1970) and available from the University of Wisconsin Genetics Computer Group (UWGCG). The preferred default parameters for the GAP program include: (1) a scoring matrix, blosum62, as described by Henikoff and Henikoff (Proc. Natl. Acad. Sci. USA 89:10915, 1992); (2) a gap weight of 12; (3) a gap length weight of 4; and (4) no penalty for end gaps. Other programs used by one skilled in the art of sequence comparison may also be used.

The variants of the invention include, for example, those that result from alternate mRNA splicing events or from proteolytic cleavage. Alternate splicing of mRNA may, for example, yield a truncated but biologically active protein. Variations attributable to proteolysis include, for example, differences in the N- or C-termini upon expression in different types of host cells, due to proteolytic removal of one or more terminal amino acids from the protein (generally from 1–5 terminal amino acids). Proteins in which differences in amino acid sequence are attributable to genetic polymorphism (allelic variation among individuals producing the protein) are also contemplated herein.

Additional variants within the scope of the invention include polypeptides that may be modified to create derivatives thereof by forming covalent or aggregative conjugates with other chemical moieties, such as glycosyl groups, lipids, phosphate, acetyl groups and the like. Covalent derivatives may be prepared by linking the chemical moieties to functional groups on amino acid side chains or at the N-terminus or C-terminus of a polypeptide. Conjugates comprising diagnostic (detectable) or therapeutic agents attached thereto are within the scope of the invention.

Other derivatives include covalent or aggregative conjugates of the polypeptides with other proteins or polypeptides, such as by synthesis in recombinant culture as N-terminal or C-terminal fusions. Further, fusion proteins can comprise peptides added to facilitate purification and identification. Such peptides include, for example, poly-His or the antigenic identification peptides described in U.S. Pat. No. 5,011,912 and in Hopp et al., Bio/Technology 6:1204, 1988. One such peptide is the FLAG® peptide, Asp-Tyr-Lys-Asp-Asp-Asp-Asp-Lys, which is highly antigenic and provides an epitope reversibly bound by a specific monoclonal antibody, enabling rapid assay and facile purification of expressed recombinant protein. A murine hybridoma designated 4E11 produces a monoclonal antibody that binds the FLAG® peptide in the presence of certain divalent metal cations, as described in U.S. Pat. 5,011,912, hereby incorporated by reference. The 4E11 hybridoma cell line has been deposited with the American Type Culture Collection under accession no. HB 9259. Monoclonal antibodies that bind the FLAG® peptide are available from Eastman Kodak Co., Scientific Imaging Systems Division, New Haven, Conn.

Variants include polypeptides that are substantially homologous to the native form, but which have an amino acid sequence different from that of the native form because of one or more deletions, insertions or substitutions. For example, these variants may exhibit differences in either kinase subdomain I or II. Kinase subdomain I has the consensus sequence "og-G-og-v", where uppercase letters represent invariant residues, lowercase letters represent highly conserved residues, "o" represents positions held by non polar residues, and "-" represents any amino acid. All lettering conforms to standard single letter code. "g" and "G" are Glycine and "v" is Valine. Kinase subdomain II has the consensus sequence "oaoK-o" where the same rules apply as described above, and "a" is Alanine and "K" is Lysine. Preferred variants are catalytically inactive variants of both IKR-1 and IKR-2 in which, for example, the invariant lysine residue (amino acid 38 in SEQ ID NOs:2 and 4) present in kinase subdomain II in the active site of functional kinases is substituted for an arginine or alanine residue. Additional variants encompass the substitution of invariant glycine residue (amino acid 18 in SEQ ID NOs:2 and 4) present in kinase subdomain I in the ATP binding site of kinases for any other residue.

Other particular embodiments include, but are not limited to, polypeptides that comprise from one to ten deletions, insertions or substitutions of amino acid residues, when compared to a native sequence.

A given amino acid may be replaced, for example, by a residue having similar physiochemical characteristics. Examples of such conservative substitutions include substitution of one aliphatic residue for another, such as lie, Val, Leu, or Ala for one another; substitutions of one polar residue for another, such as between Lys and Arg, Glu and Asp, or Gin and Asn; or substitutions of one aromatic residue for another, such as Phe, Trp, or Tyr for one another. Other conservative substitutions, e.g., involving substitutions of entire regions having similar hydrophobicity characteristics, are well known.

Similarly, the DNAs of the invention include variants that differ from a native DNA sequence because of one or more deletions, insertions or substitutions, but that encode a biologically active polypeptide.

In another example of variants, sequences encoding Cys residues that are not essential for biological activity can be altered to cause the Cys residues to be deleted or replaced with other amino acids, preventing formation of incorrect intramolecular disulfide bridges upon folding or renaturation.

Other variants are prepared by modification of adjacent dibasic amino acid residues, to enhance expression in yeast systems in which KEX2 protease activity is present. EP 212,914 discloses the use of site-specific mutagenesis to inactivate KEX2 protease processing sites in a protein. KEX2 protease processing sites are inactivated by deleting, adding or substituting residues to alter Arg-Arg, Arg-Lys, and Lys-Arg pairs to eliminate the occurrence of these adjacent basic residues. Lys-Lys pairings are considerably less susceptible to KEX2 cleavage, and conversion of Arg-Lys or Lys-Arg to Lys-Lys represents a conservative and preferred approach to inactivating KEX2 sites.

Production of Polypeptides and Fragments Thereof

Expression, isolation and purification of the polypeptides and fragments of the invention may be accomplished by any suitable technique, including but not limited to the following:

Expression Systems

The present invention also provides recombinant cloning and expression vectors containing DNA, as well as host cell containing the recombinant vectors. Expression vectors comprising DNA may be used to prepare the polypeptides or fragments of the invention encoded by the DNA. A method for producing polypeptides comprises culturing host cells transformed with a recombinant expression vector encoding the polypeptide, under conditions that promote expression of the polypeptide, then recovering the expressed polypeptides from the culture. The skilled artisan will recognize that the procedure for purifying the expressed polypeptides will vary according to such factors as the type of host cells employed and any particular characteristics of the polypeptide.

Any suitable expression system may be employed. The vectors include a DNA encoding a polypeptide or fragment of the invention, operably linked to suitable transcriptional or translational regulatory nucleotide sequences, such as those derived from a mammalian, microbial, viral, or insect gene. Examples of regulatory sequences include transcriptional promoters, operators, or enhancers, an mRNA ribosomal binding site, and appropriate sequences which control transcription and translation initiation and termination. Nucleotide sequences are operably linked when the regulatory sequence functionally relates to the DNA sequence. Thus, a promoter nucleotide sequence is operably linked to a DNA sequence if the promoter nucleotide sequence controls the transcription of the DNA sequence. An origin of replication that confers the ability to replicate in the desired host cells, and a selection gene by which transformants are identified, are generally incorporated into the expression vector.

In addition, a sequence encoding an appropriate signal peptide (native or heterologous) can be incorporated into expression vectors. A DNA sequence for a signal peptide (secretory leader) may be fused in frame to the nucleic acid sequence of the invention so that the DNA is initially transcribed, and the mRNA translated, into a fusion protein comprising the signal peptide. A signal peptide that is functional in the intended host cells promotes extracellular secretion of the polypeptide. The signal peptide is cleaved from the polypeptide upon secretion of polypeptide from the cell.

The skilled artisan will also recognize that the position(s) at which the signal peptide is cleaved may differ from that predicted by computer program, and may vary according to such factors as the type of host cells employed in expressing a recombinant polypeptide. A protein preparation may include a mixture of protein molecules having different N-terminal amino acids, resulting from cleavage of the signal peptide at more than one site.

Suitable host cells for expression of polypeptides include prokaryotes, yeast or higher eukaryotic cells. Mammalian or insect cells are generally preferred for use as host cells. Appropriate cloning and expression vectors for use with bacterial, fungal, yeast, and mammalian cellular hosts are described, for example, in Pouwels et al. *Cloning Vectors: A Laboratory Manual*, Elsevier, New York, (1985). Cell-free translation systems could also be employed to produce polypeptides using RNAs derived from DNA constructs disclosed herein.

Prokaryotic Systems

Prokaryotes include gram-negative or gram-positive organisms. Suitable prokaryotic host cells for transformation include, for example, *E. coli, Bacillus subtilis, Salmonella typhimurium*, and various other species within the genera *Pseudomonas, Streptomyces*, and *Staphylococcus*. In a prokaryotic host cell, such as *E. coli*, a polypeptide may include an N-terminal methionine residue to facilitate expression of the recombinant polypeptide in the prokaryotic host cell. The N-terminal Met may be cleaved from the expressed recombinant polypeptide.

Expression vectors for use in prokaryotic host cells generally comprise one or more phenotypic selectable marker genes. A phenotypic selectable marker gene is, for example, a gene encoding a protein that confers antibiotic resistance or that supplies an autotrophic requirement. Examples of useful expression vectors for prokaryotic host cells include those derived from commercially available plasmids such as the cloning vector pBR322 (ATCC 37017). pBR322 contains genes for ampicillin and tetracycline resistance and thus provides simple means for identifying transformed cells. An appropriate promoter and a DNA sequence are inserted into the pBR322 vector. Other commercially available vectors include, for example, pKK223-3 (Pharmacia Fine Chemicals, Uppsala, Sweden) and pGEM1 (Promega Biotec, Madison, Wis., USA).

Promoter sequences commonly used for recombinant prokaryotic host cell expression vectors include β-lactamase (penicillinase), lactose promoter system (Chang et al., *Nature* 275:615, 1978; and Goeddel et al., *Nature* 281:544, 1979), tryptophan (trp) promoter system (Goeddel et al., *Nucl. Acids Res.* 8:4057, 1980; and EP-A-36776) and tac promoter (Maniatis, *Molecular Cloning: A Laboratory Manual*, Cold Spring Harbor Laboratory, p. 412, 1982). A particularly useful prokaryotic host cell expression system employs a phage $\lambda P_L$ promoter and a cI857ts thermolabile repressor sequence. Plasmid vectors available from the American Type Culture Collection which incorporate derivatives of the $\lambda P_L$ promoter include plasmid pHUB2 (resident in *E. coli* strain JMB9, ATCC 37092) and pPLc28 (resident in *E. coli* RR1, ATCC Yeast Systems Alternatively, the polypeptides may be expressed in yeast host cells, preferably from the *Saccharomyces* genus (e.g., *S. cerevisiae*). Other genera of yeast, such as *Pichia* or *Kluyveromyces*, may also be employed. Yeast vectors will often contain an origin of replication sequence from a 2μ yeast plasmid, an autonomously replicating sequence (ARS), a promoter region, sequences for polyadenylation, sequences for transcription termination, and a selectable marker gene. Suitable promoter sequences for yeast vectors include, among others, promoters for metallothionein, 3-phosphoglycerate kinase (Hitzeman et al., *J. Biol. Chem.* 255:2073, 1980) or other glycolytic enzymes (Hess et al., *J. Adv. Enzyme Reg.* 7:149, 1968; and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isornerase, phospho-glucose isomerase, and glucokinase. Other suitable vectors and promoters for use in yeast expression are further described in Hitzeman, EPA-73,657. Another alternative is the glucose-repressible ADH2 promoter described by Russell et al. (*J. Biol. Chem.* 258:2674, 1982) and Beier et al. (*Nature* 300:724, 1982). Shuttle vectors replicable in both yeast and *E. coli* may be constructed by inserting DNA sequences from pBR322 for selection and replication in *E. coli* (Amp$^r$ gene and origin of replication) into the above-described yeast vectors.

The yeast α-factor leader sequence may be employed to direct secretion of the polypeptide. The α-factor leader sequence is often inserted between the promoter sequence and the structural gene sequence. See, e.g., Kurjan et al., *Cell* 30:933, 1982 and Bitter et al., *Proc. Natl. Acad. Sci. USA* 81:5330, 1984. Other leader sequences suitable for facilitating secretion of recombinant polypeptides from yeast hosts are known to those of skill in the art. A leader sequence may be modified near its 3' end to contain one or more restriction sites. This will facilitate fusion of the leader sequence to the structural gene.

Yeast transformation protocols are known to those of skill in the art. One such protocol is described by Hinnen et al., *Proc. Natl. Acad. Sci. USA* 75:1929, 1978. The Hinnen et al. protocol selects for Trp$^+$ transformants in a selective medium, wherein the selective medium consists of 0.67% yeast nitrogen base, 0.5% casamino acids, 2% glucose, 10 mg/ml adenine and 20 mg/ml uracil.

Yeast host cells transformed by vectors containing an ADH2 promoter sequence may be grown for inducing expression in a "rich" medium. An example of a rich medium is one consisting of 1% yeast extract, 2% peptone, and 1% glucose supplemented with 80 mg/ml adenine and 80 mg/ml uracil. Derepression of the ADH2 promoter occurs when glucose is exhausted from the medium.

Mammalian or Insect Systems

Mammalian or insect host cell culture systems also may be employed to express recombinant polypeptides. Baccu-lovirus systems for production of heterologous proteins in insect cells are reviewed by Luckow and Summers, *Bio/Technology* 6:47 (1988). Established cell lines of mammalian origin also may be employed. Examples of suitable mammalian host cell lines include the COS-7 line of monkey kidney cells (ATCC CRL 1651) (Gluzman et al., *Cell* 23:175, 1981), L cells, C127 cells, 3T3 cells (ATCC CCL 163), Chinese hamster ovary (CHO) cells, HeLa cells, and BHK (ATCC CRL 10) cell lines, and the CV1/EBNA cell line derived from the African green monkey kidney cell line CV1 (ATCC CCL 70) as described by McMahan et al. (*EMBO J.* 10: 2821, 1991).

Established methods for introducing DNA into mammalian cells have been described (Kaufman, R. J., *Large Scale Mammalian Cell Culture*, 1990, pp. 15–69). Additional protocols using commercially available reagents, such as Lipofectamine lipid reagent (Gibco/BRL) or Lipofectamine-Plus lipid reagent, can be used to transfect cells (Felgner et al., *Proc. Natl. Acad. Sci. USA* 84:7413–7417, 1987). In addition, electroporation can be used to transfect mammalian cells using conventional procedures, such as those in Sambrook et al. (*Molecular Cloning: A Laboratory Manual*, 2 ed. Vol. 1–3, Cold Spring Harbor Laboratory Press, 1989). Selection of stable transformants can be performed using methods known in the art, such as, for example, resistance to cytotoxic drugs. Kaufman et al., *Meth. in Enzymology* 185:487–511, 1990, describes several selection schemes, such as dihydrofolate reductase (DHFR) resistance. A suitable host strain for DHFR selection can be CHO strain DX-B11 which is deficient in DHFR (Urlaub and Chasin, *Proc. Natl. Acad. Sci. USA* 77:4216–4220, 1980). A plasmid expressing the DHFR cDNA can be introduced into strain DX-B11, and only cells that contain the plasmid can grow in the appropriate selective media. Other examples of selectable markers that can be incorporated into an expression vector include cDNAs conferring resistance to antibiotics, such as G418 and hygromycin B. Cells harboring the vector can be selected on the basis of resistance to these compounds.

Transcriptional and translational control sequences for mammalian host cell expression vectors can be excised from viral genomes. Commonly used promoter sequences and enhancer sequences are derived from polyoma virus, adenovirus 2, simian virus 40 (SV40), and human cytomegalovirus. DNA sequences derived from the SV40 viral genome, for example, SV40 origin, early and late promoter, enhancer, splice, and polyadenylation sites can be used to provide other genetic elements for expression of a structural gene sequence in a mammalian host cell. Viral early and late promoters are particularly useful because both are easily obtained from a viral genome as a fragment, which can also contain a viral origin of replication (Fiers et al., *Nature* 273:113, 1978; Kaufman, *Meth. in Enzymology*, 1990). Smaller or larger SV40 fragments can also be used, provided the approximately 250 bp sequence extending from the Hind III site toward the Bgl I site located in the SV40 viral origin of replication site is included.

Additional control sequences shown to improve expression of heterologous genes from mammalian expression vectors include such elements as the expression augmenting sequence element (EASE) derived from CHO cells (Morris et al., *Animal Cell Technology*, 1997, pp. 529–534 and PCT Application WO 97/25420) and the tripartite leader (TPL) and VA gene RNAs from Adenovirus 2 (Gingeras et al., *J. Biol. Chem.* 257:13475–13491, 1982). The internal ribosome entry site (IRES) sequences of viral origin allows dicistronic mRNAs to be translated efficiently (Oh and Sarnow, *Current Opinion in Genetics and Development* 3:295–300, 1993; Ramesh et al., *Nucleic Acids Research* 24:2697–2700, 1996). Expression of a heterologous cDNA as part of a dicistronic mRNA followed by the gene for a selectable marker (e.g. DHFR) has been shown to improve transfectability of the host and expression of the heterologous cDNA (Kaufman, *Meth. in Enzymology*, 1990). Exemplary expression vectors that employ dicistronic mRNAs are pTR-DC/GFP described by Mosser et al., *Biotechniques* 22:150–161, 1997, and p2A5I described by Morris et al., *Animal Cell Technology*, 1997, pp. 529–534.

A useful high expression vector, pCAVNOT, has been described by Mosley et al., *Cell* 59:335–348, 1989. Other expression vectors for use in mammalian host cells can be constructed as disclosed by Okayama and Berg (*Mol. Cell. Biol.* 3:280, 1983). A useful system for stable high level expression of mammalian cDNAs in C127 murine mammary epithelial cells can be constructed substantially as described by Cosman et al. (*Mol. Immunol.* 23:935, 1986). A useful high expression vector, PMLSV N1/N4, described by Cosman et al., *Nature* 312:768, 1984, has been deposited as ATCC 39890. Additional useful mammalian expression vectors are described in EP-A-0367566, and in WO 91/18982, incorporated by reference herein. In yet another alternative, the vectors can be derived from retroviruses.

Additional useful expression vectors, pFLAG® and pDC311, can also be used. FLAG® technology is centered on the fusion of a low molecular weight (1kD), hydrophilic, FLAG® marker peptide to the N-terminus of a recombinant protein expressed by pFLAG® expression vectors. pDC311 is another specialized vector used for expressing proteins in CHO cells. pDC311 is characterized by a bicistronic sequence containing the gene of interest and a dihydrofolate reductase (DHFR) gene with an internal ribosome binding site for DHFR translation, an expression augmenting sequence element (EASE), the human CMV promoter, a tripartite leader sequence, and a polyadenylation site.

Regarding signal peptides that may be employed, the choice of signal peptide or leader may depend on factors such as the type of host cells in which the recombinant polypeptide is to be produced. To illustrate, examples of heterologous signal peptides that are functional in mammalian host cells include the signal sequence for interleukin-7 (IL-7) described in U.S. Pat. No. 4,965,195; the signal sequence for interleukin-2 receptor described in Cosman et al., *Nature* 312:768 (1984); the interleukin4 receptor signal peptide described in EP 367,566; the type I interleukin-1 receptor signal peptide described in U.S. Pat. No. 4,968,607; and the type II interleukin-1 receptor signal peptide described in EP 460,846.

Purification

The invention also includes methods of isolating and purifying the polypeptides and fragments thereof.

Isolation and Purification

The "isolated" polypeptides or fragments thereof encompassed by this invention are polypeptides or fragments that are not in an environment identical to an environment in which it or they can be found in nature. The "purified" polypeptides or fragments thereof encompassed by this invention are essentially free of association with other proteins or polypeptides, for example, as a purification product of recombinant expression systems such as those described above or as a purified product from a non-recombinant source such as naturally occurring cells and/or tissues.

In one preferred embodiment, the purification of recombinant polypeptides or fragments can be accomplished using fusions of polypeptides or fragments of the invention to another polypeptide to aid in the purification of polypeptides or fragments of the invention. Such fusion partners can include the poly-His or other antigenic identification peptides described above.

With respect to any type of host cell, as is known to the skilled artisan, procedures for purifying a recombinant polypeptide or fragment will vary according to such factors as the type of host cells employed and whether or not the recombinant polypeptide or fragment is secreted into the culture medium.

In general, the recombinant polypeptide or fragment can be isolated from the host cells if not secreted, or from the medium or supernatant if soluble and secreted, followed by one or more concentration, salting-out, ion exchange, hydrophobic interaction, affinity purification or size exclusion chromatography steps. As to specific ways to accomplish these steps, the culture medium first can be concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. In addition, a chromatofocusing step can be employed. Alternatively, a hydrophobic interaction chromatography step can be employed. Suitable matrices can be phenyl or octyl moieties bound to resins. In addition, affinity chromatography with a matrix which selectively binds the recombinant protein can be employed. Examples of such resins employed are lectin columns, dye columns, and metal-chelating columns. Finally, one or more reversed-phase high performance liquid chromatography (RP-HPLC) steps employing hydrophobic RP-HPLC media, (e.g., silica gel or polymer resin having pendant methyl, octyl, octyldecyl or other aliphatic groups) can be employed to further purify the polypeptides. Some or all of the foregoing purification steps, in various combinations, are well known and can be employed to provide an isolated and purified recombinant protein.

It is also possible to utilize an affinity column comprising a polypeptide-binding protein of the invention, such as a monoclonal antibody generated against polypeptides of the invention, to affinity-purify expressed polypeptides. These polypeptides can be removed from an affinity column using conventional techniques, e.g., in a high salt elution buffer and then dialyzed into a lower salt buffer for use or by changing pH or other components depending on the affinity matrix utilized, or be competitively removed using the naturally occurring substrate of the affinity moiety, such as a polypeptide derived from the invention.

In this aspect of the invention, polypeptide-binding proteins, such as the anti-polypeptide antibodies of the invention or other proteins that may interact with the polypeptide of the invention, can be bound to a solid phase support such as a column chromatography matrix or a similar substrate suitable for identifying, separating, or purifying cells that express polypeptides of the invention on their surface. Adherence of polypeptide-binding proteins of the invention to a solid phase contacting surface can be accomplished by any means, for example, magnetic microspheres can be coated with these polypeptide-binding proteins and held in the incubation vessel through a magnetic field. Suspensions of cell mixtures are contacted with the solid phase that has such polypeptide-binding proteins thereon. Cells having polypeptides of the invention on their surface bind to the fixed polypeptide-binding protein and unbound cells then are washed away. This affinity-binding method is useful for purifying, screening, or separating such polypeptide-expressing cells from solution. Methods of releasing positively selected cells from the solid phase are known in the art and encompass, for example, the use of enzymes. Such enzymes are preferably non-toxic and non-injurious to the cells and are preferably directed to cleaving the cell-surface binding partner.

Alternatively, mixtures of cells suspected of containing polypeptide-expressing cells of the invention first can be incubated with a biotinylated polypeptide-binding protein of the invention. Incubation periods are typically at least one hour in duration to ensure sufficient binding to polypeptides of the invention. The resulting mixture then is passed through a column packed with avidin-coated beads, whereby the high affinity of biotin for avidin provides the binding of the polypeptide-binding cells to the beads. Use of avidin-coated beads is known in the art. See Berenson, et al. *J. Cell. Biochem.*, 10D:239 (1986). Wash of unbound material and the release of the bound cells is performed using conventional methods.

The desired degree of purity depends on the intended use of the protein. A relatively high degree of purity is desired when the polypeptide is to be administered in vivo, for example, In such a case, the polypeptides are purified such that no protein bands corresponding to other proteins are detectable upon analysis by SDS-polyacrylamide gel electrophoresis (SDS-PAGE). It will be recognized by one skilled in the pertinent field that multiple bands corresponding to the polypeptide may be visualized by SDS-PAGE, due to differential glycosylation, differential post-translational processing, and the like. Most preferably, the polypeptide of the invention is purified to substantial homogeneity, as indicated by a single protein band upon analysis by SDS- PAGE. The protein band may be visualized by silver staining, Coomassie blue staining, or (if the protein is radiolabeled) by autoradiography.

Use of IKR Nucleic Acid of Oligonucleotides

In addition to being used to express polypeptides as described above, the nucleic acids of the invention, including DNA and oligonucleotides thereof, can be used as probes to identify other nucleic acids encoding proteins having kinsase activity.

Among the uses of nucleic acids of the invention is the use of fragments thereof as probes or primers to aid in the isolation of other proteins having kinase activity. Such fragments generally comprise at least about 17 contiguous nucleotides of a DNA sequence. In other embodiments, a DNA fragment comprises at least 30, or at least 60, contiguous nucleotides of a DNA sequence.

Because homologs of SEQ ID NOs:1 and 2, from other mammalian species are contemplated herein, probes based on the murine DNA sequence of SEQ ID NOs:1 and 2 may be used to screen cDNA libraries derived from other mammalian species, using conventional cross-species hybridization techniques.

Using knowledge of the genetic code in combination with the amino acid sequences set forth above, sets of degenerate oligonucleotides can be prepared. Such oligonucleotides are useful as primers, e.g., in polymerase chain reactions (PCR), whereby DNA fragments are isolated and amplified.

Use of IKR Polypeptides and Fragmented Polypeptides

Uses include, but are not limited to, the following:

Purifying proteins and measuring activity thereof

Research Reagents

Molecular weight and Isoelectric focusing markers

Controls for peptide fragmentation

Identification of unknown proteins

Preparation of Antibodies

Purification Reagents

Each of the polypeptides of the invention finds use as a protein purification reagent. For example, the polypeptides may be used to purify binding partner proteins, such as naturally occurring substrates or protein inhibitors, which bind specifically to the catalytic site of either IKR-1 or IKR-2. In addition, both IKR-1 and IKR-2 might also serve as substrates for other kinases in a kinase cascade, such as kinases that bind to and modulate the activity of or cellular localization of IKR-1 or IKR-2. Therefore they might be used to bind and facilitate purification of these other kinases and proteins.

In particular embodiments, a polypeptide (in any form described herein that is capable of binding a binding partner) is attached to a solid support by conventional procedures. As one example, affinity chromatography columns containing functional groups that will react with functional groups on amino acid side chains of proteins are available (Pharmacia Biotech, Inc., Piscataway, N.J.). In an alternative, a polypeptide/Fc protein (as discussed above) is attached to Protein A- or Protein G-containing chromatography columns through interaction with the Fc moiety.

Measuring Activity

Polypeptides also find use in measuring the biological activity of binding partner proteins in terms of their binding affinity. The polypeptides thus may be employed by those conducting "quality assurance" studies, e.g., to monitor shelf life and stability of protein under different conditions. For example, the polypeptides may be employed in a binding affinity study to measure the biological activity of a binding partner protein that has been stored at different temperatures, or produced in different cell types. The proteins also may be used to determine whether biological activity is retained after modification of a binding partner protein (e.g., chemical modification, truncation, mutation, etc.). The binding affinity of the modified binding partner protein is compared to that of an unmodified binding partner protein to detect any adverse impact of the modifications on biological activity of the binding partner. The biological activity of a binding partner protein thus can be ascertained before it is used in a research study, for example.

In a particularly preferred embodiment, the polypeptides, fragments or fusion proteins thereof can be used to assay protein kinase activity.

Research Agents

Polypeptides of the invention may be used to set up screening assays to identify molecules from, for example, chemical libraries, combinatorial chemistry libraries, natural product libraries or other libraries of small organic molecules that inhibit or activate IKR-1 and/or IKR-2 activity. Such a small molecule antagonist or agonist could be useful in disrupting or enhancing molecular signaling to certain transcriptional activators.

Another embodiment of the invention is the use of isolated IKR-1 or IKR-2 polypeptides, fusion proteins, or a fragment thereof containing the isolated protein kinase domain of IKR-1 or IKR-2 in in vitro or in vivo assays to determine protein kinase activity. A hallmark of protein kinases is their ability to phosphorylate other proteins and to auto-phosphorylate. Therefore, in one aspect of the invention, the isolated polypeptides with kinase activity can be used in assays to phosphorylate target proteins, radiolabel target proteins with $^{32}p$, and identify proteins having phosphatase activity. Exemplary methods of phosphorylation assays set forth above are disclosed in U.S. Pat. No. 5,447,860 which is incorporated herein by reference. In addition to full length polypeptides, the invention also includes the isolated active kinase domains of kinases which can function as reagents in kinase assays.

Kinase assays are typically carried out by combining IKR-1, IKR-2, or an active kinase domain with radiolabeled ATP ($\gamma^{32}P$-ATP) and a peptide or protein substrate in a buffer solution. The peptide substrates generally range from 8 to 30 amino acids in length or the substrate may also be a protein known to be phosphorylated readily by IKR-1 and/or IKR-2. Many such general kinase substrates are known, such as α or β casein, histone H1, myelin basic protein, etc. After incubation of this reaction mixture at 20–37° C. for a suitable time, the kinase-mediated transfer of radioactive phosphate from ATP to the substrate protein or substrate peptide can be determined by methods well known in the art.

The purpose of such an assay would be to identify substances which interfere with the rate of substrate phosphorylation. Such inhibitory substances could serve as lead compounds in the development of pharmaceuticals for the treatment of autoimmune, inflammatory, infectious or neoplastic diseases in which there is a disregulation of the inflammatory processes mediated by IKR-1 or IKR-2. It is conceivable that compounds which inhibit IKR-1 or IKR-2 could have merit as more general inhibitors of the class of protein kinases which mediate the inflammatory process, including (but not limited to) those mentioned above.

Yet another embodiment of the invention relates to the use of IKR polypeptides and fragments as reagents to identify (a) any protein that the polypeptide regulates, and (b) other proteins with which it might interact. Thus, IKR-1 and IKR-2 can be used to study, for example, cell signal transduction.

The IKRs, like other I kappa B kinases, could play a central role in immune responses which includes cellular signal transduction and inflammatory responses. As such, alterations in the expression and/or activation of IKR-1 and/or IKR-2 can have profound effects on a plethora of cellular processes. Expression of cloned IKR-1 and/or IKR-2, functionally inactive mutants of IKR-1 and/or IKR-2, or the kinase domain can be used to identify the role a particular protein plays in mediating specific signaling events.

Cellular signaling often involves a molecular activation cascade, during which a receptor propagates a ligand-receptor mediated signal by specifically activating intracellular kinases which phosphorylate target substrates, ultimately resulting in the activation of the transcription factor NFkB and/or other transcription factors. These substrates can themselves be kinases which become activated following phosphorylation. Alternatively, they can be adaptor molecules that facilitate down stream signaling through protein-protein interaction following phosphorylation. Regardless of the nature of the substrate molecule(s), expressed functionally-active versions of IKR-1 and/or IKR-2, for example the IKR kinase domain, can be used in assays such as the yeast 2-hybrid assay to identify what substrate(s) were recognized and altered by IKR-1 and/or IKR-2. As such, these novel IKR-1 or IKR-2 polypeptides can be used as reagents to identify novel molecules involved in signal transduction pathways. In addition, IKR-1, IKR-2, and other downstream molecules involved in the signal transduction pathway can be potential targets for therapeutic compounds that interfere with the activation of NF-κB.

Molecular Weight, Isoelectric Point Markers

The polypeptides of the present invention can be subjected to fragmentation into smaller peptides by chemical and enzymatic means, and the peptide fragments so produced can be used in the analysis of other proteins or polypeptides. For example, such peptide fragments can be used as peptide molecular weight markers, peptide isoelectric point markers, or in the analysis of the degree of peptide fragmentation. Thus, the invention also includes these polypeptides and peptide fragments, as well as kits to aid in the determination of the apparent molecular weight and isoelectric point of an unknown protein and kits to assess the degree of fragmentation of an unknown protein.

Although all methods of fragmentation are encompassed by the invention, chemical fragmentation is a preferred embodiment, and includes the use of cyanogen bromide to cleave under neutral or acidic conditions such that specific cleavage occurs at methionine residues (E. Gross, *Methods in Enz.* 11:238–255, 1967). This can further include additional steps, such as a carboxymethylation step to convert cysteine residues to an unreactive species.

Enzymatic fragmentation is another preferred embodiment, and includes the use of a protease such as Asparaginylendo-peptidase, Arginylendo-peptidase, *Achromobacter* protease I, Trypsin, *Staphlococcus aureus* V8 protease, Endoproteinase Asp-N, or Endoproteinase Lys-C under conventional conditions to result in cleavage at specific amino acid residues. Asparaginylendo-peptidase can cleave specifically on the carboxyl side of the asparagine residues present within the polypeptides of the invention. Arginylendo-peptidase can cleave specifically on the carboxyl side of the arginine residues present within these polypeptides. *Achromobacter* protease I can cleave specifically on the carboxyl side of the lysine residues present within the polypeptides (Sakiyama and Nakat, U.S. Pat. No. 5,248,599; T. Masaki et al., *Biochim. Biophys. Acta* 660:44–50, 1981; T. Masaki et al., *Biochim. Biophys. Acta* 660:51–55, 1981). Trypsin can cleave specifically on the carboxyl side of the arginine and lysine residues present within polypeptides of the invention. Enzymatic fragmentation may also occur with a protease that cleaves at multiple amino acid residues. For example, *Staphlococcus aureus* V8 protease can cleave specifically on the carboxyl side of the aspartic and glutamic acid residues present within polypeptides (D. W. Cleveland, *J. Biol. Chem.* 3:1102–1106, 1977). Endoproteinase Asp-N can cleave specifically on the amino side of the asparagine residues present within polypeptides. Endoproteinase Lys-C can cleave specifically on the carboxyl side of the lysine residues present within polypeptides of the invention. Other enzymatic and chemical treatments can likewise be used to specifically fragment these polypeptides into a unique set of specific peptides.

Of course, the peptides and fragments of the polypeptides of the invention can also be produced by conventional recombinant processes and synthetic processes well known in the art. With regard to recombinant processes, the polypeptides and peptide fragments encompassed by invention can have variable molecular weights, depending upon the host cell in which they are expressed.

The molecular weight of these polypeptides can also be varied by fusing additional peptide sequences to both the amino and carboxyl terminal ends of polypeptides of the invention. Fusions of additional peptide sequences at the amino and carboxyl terminal ends of polypeptides of the invention can be used to enhance expression of these polypeptides or aid in the purification of the protein. In addition, fusions of additional peptide sequences at the amino and carboxyl terminal ends of polypeptides of the invention will alter some, but usually not all, of the fragmented peptides of the polypeptides generated by enzymatic or chemical treatment. Of course, mutations can be introduced into polypeptides of the invention using routine and known techniques of molecular biology. For example, a mutation can be designed so as to eliminate a site of proteolytic cleavage by a specific enzyme or a site of cleavage by a specific chemically induced fragmentation procedure. The elimination of the site will alter the peptide fingerprint of polypeptides of the invention upon fragmentation with the specific enzyme or chemical procedure.

Because the unique amino acid sequence of each piece specifies a molecular weight, these pieces can thereafter serve as molecular weight markers using such analysis techniques to assist in the determination of the molecular weight of an unknown protein, polypeptides or fragments thereof. The molecular weight markers of the invention serve particularly welt as molecular weight markers for the estimation of the apparent molecular weight of proteins that have similar apparent molecular weights and, consequently, allow increased accuracy in the determination of apparent molecular weight of proteins.

When the invention relates to the use of fragmented peptide molecular weight markers, those markers are preferably at least 10 amino acids in size. More preferably, these fragmented peptide molecular weight markers are between 10 and 100 amino acids in size. Even more preferable are fragmented peptide molecular weight markers between 10 and 50 amino acids in size and especially between 10 and 35 amino acids in size. Most preferable are fragmented peptide molecular weight markers between 10 and 20 amino acids in size.

Among the methods for determining molecular weight are sedimentation, gel electrophoresis, chromatography, and mass spectrometry. A particularly preferred embodiment is denaturing polyacrylamide gel electrophoresis (U. K. Laemmli, *Nature* 227:680–685, 1970). Conventionally, the method uses two separate lanes of a gel containing sodium dodecyl sulfate and a concentration of acrylamide between 6–20%. The ability to simultaneously resolve the marker and the sample under identical conditions allows for increased accuracy. It is understood, of course, that many different techniques can be used for the determination of the molecular weight of an unknown protein using polypeptides of the invention, and that this embodiment in no way limits the scope of the invention.

Each polypeptide or fragment thereof has a pI that is intrinsically determined by its unique amino acid sequence (which pI can be estimated by the skilled artisan using any of the computer programs designed to predict pI values currently available, calculated using any well-known known amino acid pKa table, or measured empirically). Therefore these polypeptides and fragments thereof can serve as specific markers to assist in the determination of the isoelectric point of an unknown protein, polypeptide, or fragmented peptide using techniques such as isoelectric focusing. These polypeptide or fragmented peptide markers serve particularly well for the estimation of apparent isoelectric points of unknown proteins that have apparent isoelectric points close to that of the polypeptide or fragmented peptide markers of the invention.

The technique of isoelectric focusing can be further combined with other techniques such as gel electrophoresis to simultaneously separate a protein on the basis of molecular weight and charge. The ability to simultaneously resolve these polypeptide or fragmented peptide markers and the unknown protein under identical conditions allows for increased accuracy in the determination of the apparent isoelectric point of the unknown protein. This is of particular interest in techniques, such as two dimensional electrophoresis (T. D. Brock and M. T. Madigan, *Biology of Microorganisms* 76–77 (Prentice Hall, 6d ed. 1991)), where the nature of the procedure dictates that any markers should be resolved simultaneously with the unknown protein. In addition, with such methods, these polypeptides and fragmented peptides thereof can assist in the determination of both the isoelectric point and molecular weight of an unknown protein or fragmented peptide.

Polypeptides and fragmented peptides can be visualized using two different methods that allow a discrimination between the unknown protein and the molecular weight markers. In one embodiment, the polypeptide and fragmented peptide molecular weight markers of the invention can be visualized using antibodies generated against these markers and conventional immunoblotting techniques. This detection is performed under conventional conditions that do not result in the detection of the unknown protein. It is understood that it may not be possible to generate antibodies against all polypeptide fragments of the invention, since small peptides may not contain immunogenic epitopes. It is further understood that not all antibodies will work in this assay; however, those antibodies which are able to bind polypeptides and fragments of the invention can be readily determined using conventional techniques.

The unknown protein is also visualized by using a conventional staining procedure. The molar excess of unknown protein to polypeptide or fragmented peptide molecular weight markers of the invention is such that the conventional staining procedure predominantly detects the unknown protein. The level of these polypeptide or fragmented peptide molecular weight markers is such as to allow little or no detection of these markers by the conventional staining method. The preferred molar excess of unknown protein to polypeptide molecular weight markers of the invention is between 2 and 100,000 fold. More preferably, the preferred molar excess of unknown protein to these polypeptide molecular weight markers is between 10 and 10,000 fold and especially between 100 and 1,000 fold.

It is understood of course that many techniques can be used for the determination and detection of molecular weight and isoelectric point of an unknown protein, polypeptides, and fragmented peptides thereof using these polypeptide molecular weight markers and peptide fragments thereof and that these embodiments in no way limit the scope of the invention.

In another embodiment, the analysis of the progressive fragmentation of the polypeptides of the invention into specific peptides (D. W. Cleveland et al., *J. Biol. Chem.* 252:1102–1106, 1977), such as by altering the time or temperature of the fragmentation reaction, can be used as a control for the extent of cleavage of an unknown protein. For example, cleavage of the same amount of polypeptide and unknown protein under identical conditions can allow for a direct comparison of the extent of fragmentation. Conditions that result in the complete fragmentation of the polypeptide can also result in complete fragmentation of the unknown protein.

As to the specific use of the polypeptides and fragmented peptides of the invention as molecular weight markers, the fragmentation of the polypeptide of SEQ ID NOs:3 and 4 with cyanogen bromide generates a unique set of fragmented peptide molecular weight markers with the molecular weights shown in Table I. The distribution of methionine residues determines the number of amino acids in each peptide and the unique amino acid composition of each peptide determines its molecular weight.

TABLE I

Cleavage of IKR-1 and IKR-2 with cyanogen bromide

| Fragment # | Residues | Avg. MW |
|---|---|---|
| | IKR- 1 | |
| 1 | 1–1 | 101.10 |
| 2 | 685–691 | 803.85 |
| 3 | 554–565 | 1564.85 |
| 4 | 670–684 | 1609.81 |
| 5 | 124–142 | 2165.45 |
| 6 | 670–691 | 2443.75 |
| 7 | 692–717 | 3030.49 |
| 8 | 685–717 | 3864.43 |
| 9 | 87–123 | 3975.47 |
| 10 | 235–271 | 4088.61 |
| 11 | 143–184 | 4761.19 |
| 12 | 185–234 | 5569.46 |
| 13 | 566–614 | 5751.57 |
| 14 | 385–441 | 6027.92 |
| 15 | 615–669 | 6032.69 |
| 16 | 87–142 | 6171.01 |
| 17 | 124–184 | 6956.73 |
| 18 | 554–614 | 7346.52 |
| 19 | 615–684 | 7672.59 |
| 20 | 2–86 | 9613.92 |
| 21 | 185–271 | 9688.16 |
| 22 | 1–86 | 9745.12 |
| 23 | 143–234 | 10360.74 |
| 24 | 566–669 | 11814.35 |
| 25 | 272–384 | 12699.43 |
| 26 | 442–553 | 12715.48 |
| 27 | 2–123 | 13619.48 |
| 28 | 442–565 | 14310.42 |
| 29 | 235–384 | 16818.13 |

TABLE I-continued

Cleavage of IKR-1 and IKR-2 with cyanogen bromide

| Fragment # | Residues | Avg. MW |
|---|---|---|
| 30 | 272–441 | 18757.45 |
| 31 | 385–553 | 18773.50 |
| IKR-2 | | |
| 1 | 1–1 | 101.10 |
| 2 | 687–690 | 372.42 |
| 3 | 621–623 | 385.47 |
| 4 | 691–697 | 857.02 |
| 5 | 663–673 | 993.13 |
| 6 | 720–729 | 1061.19 |
| 7 | 310–319 | 1162.36 |
| 8 | 687–697 | 1259.53 |
| 9 | 674–686 | 1373.52 |
| 10 | 674–690 | 1776.04 |
| 11 | 124–142 | 2165.45 |
| 12 | 663–686 | 2396.75 |
| 13 | 698–719 | 2438.73 |
| 14 | 415–439 | 2657.14 |
| 15 | 599–620 | 2717.95 |
| 16 | 599–623 | 3133.51 |
| 17 | 691–719 | 3325.84 |
| 18 | 698–729 | 3530.01 |
| 19 | 54–86 | 3960.69 |
| 20 | 87–123 | 3987.52 |
| 21 | 624–662 | 4679.24 |
| 22 | 143–184 | 4776.11 |
| 23 | 621–662 | 5094.80 |
| 24 | 440–486 | 5632.61 |
| 25 | 624–673 | 5702.47 |
| 26 | 185–234 | 5762.53 |
| 27 | 2–53 | 5796.60 |
| 28 | 1–53 | 5927.80 |
| 29 | 87–142 | 6183.06 |
| 30 | 124–184 | 6971.66 |
| 31 | 54–123 | 7978.30 |
| 32 | 235–309 | 8078.16 |
| 33 | 415–486 | 8319.85 |
| 34 | 235–319 | 9270.61 |
| 35 | 2–86 | 9787.38 |
| 36 | 143–234 | 10568.74 |
| 37 | 320–414 | 10981.47 |
| 38 | 310–414 | 12173.92 |
| 39 | 487–598 | 12852.49 |
| 40 | 320–439 | 13668.70 |
| 41 | 185–309 | 13870.79 |
| 42 | 487–620 | 15600.53 |
| 43 | 440–598 | 18515.20 |

In addition, the preferred purified polypeptides of the invention (SEQ ID NOs:3 and 4) have a calculated molecular weight of approximately 80,962 and 83,425 Daltons, respectively, and use thereof allows increased accuracy in the determination of apparent molecular weight of proteins that have apparent molecular weights close to 80,962 or 83,425 Daltons.

Finally, as to the kits that are encompassed by the invention, the constituents of such kits can be varied, but typically contain the polypeptide and fragmented peptide molecular weight markers. Also, such kits can contain the polypeptides wherein a site necessary for fragmentation has been removed. Furthermore, the kits can contain reagents for the specific cleavage of the polypeptide and the unknown protein by chemical or enzymatic cleavage. Kits can further contain antibodies directed against polypeptides or fragments thereof of the invention.

Identification of Unknown Proteins

As set forth above, a polypeptide or peptide fingerprint can be entered into or compared to a database of known proteins to assist in the identification of the unknown protein using mass spectrometry (W. J. Henzel et al., Proc. Natl. Acad. Sci. USA 90:5011–5015, 1993; D. Fenyo et al., Electrophoresis 19:998–1005, 1998). A variety of computer software programs to facilitate these comparisons are accessible via the Internet, such as Protein Prospector (prospector.uscf.edu), Multildent (expasy.ch/sprot/multiident.html), PeptideSearch (mann.embl-heiedelberg.de/deSearch/FR_PeptideSearchForrn.html), and ProFound (chait-sgi.rockefeller.edu/cgi-bin/prot-id-frag.html). These programs allow the user to specify the cleavage agent and the molecular weights of the fragmented peptides within a designated tolerance. The programs compare observed molecular weights to predicted peptide molecular weights derived from sequence databases to assist in determining the identity of the unknown protein.

In addition, a polypeptide or peptide digest can be sequenced using tandem mass spectrometry (MS/MS) and the resulting sequence searched against databases (J. K. Eng, et al., J. Am. Soc. Mass Spec. 5:976–989 (1994); M. Mann and M. Wilm, Anal. Chem. 66:4390–4399 (1994); J. A. Taylor and R. S. Johnson, Rapid Comm. Mass Spec. 11: 1067–1075 (1997)). Searching programs that can be used in this process exist on the Internet, such as Lutefisk 97 (lsbc.com:70/Lutefisk97.html), and the Protein Prospector, Peptide Search and ProFound programs described above.

Therefore, adding the sequence of a gene and its predicted protein sequence and peptide fragments to a sequence database can aid in the identification of unknown proteins using mass spectrometry.

Antibodies

Antibodies that are immunoreactive with the polypeptides of the invention are provided herein. Such antibodies specifically bind to the polypeptides via the antigen-binding sites of the antibody (as opposed to non-specific binding). Thus, the polypeptides, fragments, variants, fusion proteins, etc., as set forth above may be employed as "immunogens" in producing antibodies immunoreactive therewith. More specifically, the polypeptides, fragment, variants, fusion proteins, etc. contain antigenic determinants or epitopes that elicit the formation of antibodies.

These antigenic determinants or epitopes can be either linear or conformational (discontinuous). Linear epitopes are composed of a single section of amino acids of the polypeptide, while conformational or discontinuous epitopes are composed of amino acids sections from different regions of the polypeptide chain that are brought into close proximity upon protein folding (C. A. Janeway, Jr. and P. Travers, *Immuno Biology* 3:9 (Garland Publishing Inc., 2nd ed. 1996)). Because folded proteins have complex surfaces, the number of epitopes available is quite numerous; however, due to the conformation of the protein and steric hinderances, the number of antibodies that actually bind to the epitopes is less than the number of available epitopes (C. A. Janeway, Jr. and P. Travers, *Immuno Biology* 2:14 (Garland Publishing Inc., 2nd ed. 1996)). Epitopes may be identified by any of the methods known in the art.

Thus, one aspect of the present invention relates to the antigenic epitopes of the polypeptides of the invention. Such epitopes are useful for raising antibodies, in particular monoclonal antibodies, as described in more detail below. Additionally, epitopes from the polypeptides of the invention can be used as research reagents, in assays, and to purify specific binding antibodies from substances such as polyclonal sera or supernatants from cultured hybridomas. Such epitopes or variants thereof can be produced using techniques well known in the art such as solid-phase synthesis, chemical or enzymatic cleavage of a polypeptide, or using recombinant DNA technology.

As to the antibodies that can be elicited by the epitopes of the polypeptides of the invention, whether the epitopes have been isolated or remain part of the polypeptides, both polyclonal and monoclonal antibodies may be prepared by conventional techniques. See, for example, *Monoclonal Antibodies, Hybridomas: A New Dimension in Biological Analyses,* Kennet et al. (eds.), Plenum Press, New York (1980); and *Antibodies: A Laboratory Manual,* Harlow and Land (eds.), Cold Spring Harbor Laboratory Press, Cold Spring Harbor, N.Y., (1988).

Hybridoma cell lines that produce monoclonal antibodies specific for the polypeptides of the invention are also contemplated herein. Such hybridomas may be produced and identified by conventional techniques. One method for producing such a hybridoma cell line comprises immunizing an animal with a polypeptide; harvesting spleen cells from the immunized animal; fusing said spleen cells to a myeloma cell line, thereby generating hybridoma cells; and identifying a hybridoma cell line that produces a monoclonal antibody that binds the polypeptide. The monoclonal antibodies may be recovered by conventional techniques.

The monoclonal antibodies of the present invention also include chimeric antibodies, e.g., humanized versions of murine monoclonal antibodies. Such humanized antibodies may be prepared by known techniques and offer the advantage of reduced immunogenicity when the antibodies are administered to humans. In one embodiment, a humanized monoclonal antibody comprises the variable region of a murine antibody (or just the antigen binding site thereof) and a constant region derived from a human antibody. Alternatively, a humanized antibody fragment may comprise the antigen binding site of a murine monoclonal antibody and a variable region fragment (lacking the antigen-binding site) derived from a human antibody. Procedures for the production of chimeric and further engineered monoclonal antibodies include those described in Riechmann et al. (*Nature* 332:323, 1988), Liu et al. (*PNAS* 84:3439, 1987), Larrick et al. (*Bio/Technology* 7:934, 1989), and Winter and Harris (TIPS 14:139, May, 1993). Procedures to generate antibodies transgenically can be found in GB 2,272,440, U.S. Pat. Nos. 5,569,825 and 5,545,806 and related patents claiming priority therefrom, all of which are incorporated by reference herein.

Antigen-binding fragments of the antibodies, which may be produced by conventional techniques, are also encompassed by the present invention. Examples of such fragments include, but are not limited to, Fab and F(ab')$_2$ fragments. Antibody fragments and derivatives produced by genetic engineering techniques are also provided.

In one embodiment, the antibodies are specific for the polypeptides of the present invention and do not cross-react with other proteins. Screening procedures by which such antibodies may be identified are well known, and may involve immunoaffinity chromatography, for example.

Uses Thereof

The antibodies of the invention can be used in assays to detect the presence of the polypeptides or fragments of the invention, either in vitro or in vivo. The antibodies also may be employed in purifying polypeptides or fragments of the invention by immunoaffinity chromatography.

Those antibodies that additionally can block binding of the polypeptides of the invention to the binding partner(s) may be used to inhibit a biological activity that results from such binding. Such blocking antibodies may be identified using any suitable assay procedure, such as by testing antibodies for the ability to inhibit binding of IKR-1 and/or IKR-2 to the binding partner(s). Alternatively, blocking antibodies may be identified in assays for the ability to inhibit a biological effect that results from binding of IKR-1 and/or IKR-2 to its binding partner(s).

Such an antibody may be employed in an in vitro procedure, or administered in vivo to inhibit a biological activity mediated by the entity that generated the antibody. Disorders caused or exacerbated (directly or indirectly) by the interaction of IKR-1 and/or IKR-2 with a binding partner thus may be treated. A therapeutic method involves in vivo administration of a blocking antibody in an intracellular form to a mammal in an amount effective in inhibiting an IKR-1 and/or IKR-2-mediated biological activity. Monoclonal antibodies are generally preferred for use in such therapeutic methods.

Antibodies may be screened for agonistic (i.e., ligand-mimicking) properties. Such antibodies, upon binding to IKR-1 and/or IKR-2 binding partner(s), induce biological effects (e.g., transduction of biological signals) similar to the biological effects induced when IKR-1 or IKR-2 binds to a binding partner.

Furthermore, antibodies may be used to specifically immunoprecipitate IKR-1 and /or IKR-2. Such immnunoprecipitates can be captured by procedures known in the art, such as binding to resin attached Protein A. The resultant resin bound complex can be utilized as a source of kinase for in vitro kinase $^{32}$P phosphotransferase assays as described above.

Compositions comprising an antibody that is directed against IKR-1 and/or IKR-2, and a physiologically acceptable diluent, excipient, or carrier, are provided herein. Suitable components of such compositions are as described above for compositions containing IKR-1, IKR-2, IKR-1 binding partner proteins, or IKR-2 binding partner proteins.

Also provided herein are conjugates comprising a detectable (e.g., diagnostic) or therapeutic agent, attached to the antibody. Examples of such agents are presented above. The conjugates find use in in vitro or in vivo procedures.

The following examples are provided to further illustrate particular embodiments of the invention, and are not to be construed as limiting the scope of the present invention.

EXAMPLE 1

Isolation of the Nucleic Acid

The original cDNA clone from which the sequences are derived was obtained from a murine transit amplifying cell (TRAM) library that is maintained by Genesis. Independent clones for both IKR-1 and IKR-2 were obtained from the murine T-cell line bacteriophage library, EL46.1N7ZAP. In the case of IKR-1, three independent clones were isolated and required to obtain full length sequence, whereas a single full length IKR-2 clone was isolated. Full length sequences for the novel protein kinases IKR-1 (SEQ ID NO:1) and IKR-2 (SEQ ID NO:3) are shown above.

IKR-1 (SEQ ID NO:1) contains 5' and 3' untranslated sequence and the coding region consisting of nucleotides 369–2520, and IKR-2 (SEQ ID NO:3) also contains 5' and 3' untranslated sequence and the coding region consisting of nucleotides 212–2398. SEQ ID NOs:2 and 4 show translated full length open reading frames for IKR-1 and IKR-2, respectively.

EXAMPLE 2

Use of IKR Polypeptides in an ELISA

Serial dilutions of IKR-containing samples (in 50 mM NaHCO$_3$, brought to pH 9 with NaOH) are coated onto Linbro/Titertek 96 well flat bottom E.I.A. microtitration plates (ICN Biomedicals Inc., Aurora, Ohio) at 100:1/well. After incubation at 4° C. for 16 hours, the wells are washed six times with 200:1 PBS containing 0.05% Tween-20 (PBS-Tween). The wells are then incubated with FLAG®-IKR binding partner at 1 µg/ml in PBS-Tween with 5% fetal calf serum (FCS) for 90 minutes (100:1 per well), followed by washing as above. Next, each well is incubated with the anti-FLAG® (monoclonal antibody M2 at 1 µg/ml in PBS-Tween containing 5% FCS for 90 minutes (100:1 per well), followed by washing as above. Subsequently, wells are incubated with a polyclonal goat anti-mIgG1-specific horseradish peroxidase-conjugated antibody (a 1:5000 dilution of the commercial stock in PBS-Tween containing 5% FCS) for 90 minutes (100:1 per well). The HRP-conjugated antibody is obtained from Southern Biotechnology Associates, Inc., Birmingham, Ala. Wells then are washed six times, as above.

For development of the ELISA, a substrate mix [100:1 per well of a 1:1 premix of the TMB Peroxidase Substrate and Peroxidase Solution B (Kirkegaard Perry Laboratories, Gaithersburg, Md.)] is added to the wells. After sufficient color reaction, the enzymatic reaction is terminated by addition of 2 N H$_2$SO$_4$ (50:1 per well). Color intensity (indicating IKR-1 and/or IKR-2-binding activity) is determined by measuring extinction at 450 nm on a V Max plate reader (Molecular Devices, Sunnyvale, Calif.).

EXAMPLE 3

Monoclonal Antibodies That Bind

This example illustrates a method for preparing monoclonal antibodies that bind IKR-1 and/or IKR-2 polypeptides. Suitable immunogens that may be employed in generating such antibodies include, but are not limited to, purified IKR-1 and/or IKR-2 polypeptides or an immunogenic fragment thereof.

Purified IKR-1 and/or IKR-2 can be used to generate monoclonal antibodies immunoreactive therewith, using conventional techniques such as those described in U.S. Pat. No. 4,411,993. Briefly, mice are immunized with IKR-1 and/or IKR-2 immunogen emulsified in complete Freund's adjuvant, and injected in amounts ranging from 10–100 :g subcutaneously or intraperitoneally. Ten to twelve days later, the immunized animals are boosted with additional IKR-1 and/or IKR-2 emulsified in incomplete Freund's adjuvant. Mice are periodically boosted thereafter on a weekly to bi-weekly immunization schedule. Serum samples are periodically taken by retro-orbital bleeding or tail-tip excision to test for IKR-1 and/or IKR-2 antibodies by dot blot assay, ELISA (Enzyme-Linked Immunosorbent Assay), inhibition of IKR-1 and/or IKR-2-binding partner binding, or inhibition of kinase catalytic activity.

Following detection of an appropriate antibody titer, positive animals are provided one last intravenous injection of IKR-1 and/or IKR-2 in saline. Three to four days later, the animals are sacrificed, spleen cells harvested, and spleen cells are fused to a murine myeloma cell line, e.g., NS1 or preferably P3x63Ag8.653 (ATCC CRL 1580). Fusions generate hybridoma cells, which are plated in multiple microtiter plates in a HAT (hypoxanthine, aminopterin and thymidine) selective medium to inhibit proliferation of non-fused cells, myeloma hybrids, and spleen cell hybrids.

The hybridoma cells are screened by ELISA for reactivity against purified IKR-1 and/or IKR-2 by adaptations of the techniques disclosed in Engvall et al., *Immunochem.* 8:871, 1971 and in U.S. Pat. No. 4,703,004. A preferred screening technique is the antibody capture technique described in Beckmann et al., (*J. Immunol.* 144:4212, 1990) Positive hybridoma cells can be injected intraperitoneally into syngeneic BALB/c mice to produce ascites containing high concentrations of anti-IKR-1 and/or IKR-2 monoclonal antibodies. Alternatively, hybridoma cells can be grown in vitro in flasks or roller bottles by various techniques. Monoclonal antibodies produced in mouse ascites can be purified by ammonium sulfate precipitation, followed by gel exclusion chromatography. Alternatively, affinity chromatography based upon binding of antibody to Protein A or Protein G can also be used, as can affinity chromatography based upon binding to IKR-1 and/or IKR-2.

EXAMPLE 4

Northern Blot Analysis

The tissue distribution of IKR-1 and IKR-2 mRNA can be investigated by Northern blot analysis, as follows. An aliquot of a radiolabeled probe ($^{32}$P-labeled PCR product derived from IKR-1 or IKR-2 specific oligonucleotide primers) is added to murine and human multiple tissue Northern blots (Clontech, Palo Alto, Calif.; Biochain, Palo Alto, Calif.). Hybridization is conducted per the manufacturer's (Clontech) protocol using their Express Hyb hybridization solution. A glycerol-aldehyde-phosphate dehydrogenase (GAPDH) specific probe can be used to standardize for RNA loadings.

Northern blot analysis and cDNA library screens suggest that both IKR-1 and IKR-2 are widely expressed.

EXAMPLE 5

Measuring Kinase Activity of IKR-1 and IKR-2

Isolated IKR-1 or IKR-2 polypeptide or fusion proteins containing the isolated protein kinase domain of IKR-1 or IKR-2 can be used in an assay of protein kinase activity. Typically this would be carried out by combining IKR-1 or IKR-2 with radiolabeled ATP ($\gamma^{32}$P-ATP) and a magnesium salt in buffer solution containing a peptide or protein substrate. The peptide substrates are generally from 8–30 amino acids in length and may terminate at the N- or C-terminus with three or more lysine or arginine residues to facilitate binding of the peptide to phosphocellulose paper. The substrate may also be a protein known to be phosphorylated readily by IKR-1 and/or IKR-2. Many such general kinase substrates are known, e.g., α or β casein, histone H1, myelin basic protein, etc. After incubation of this reaction mixture at 20–37° C. for a suitable time, the transfer of radioactive phosphate from ATP to the substrate protein or substrate peptide may be monitored, by spotting of the reaction mixture onto phosphocellulose paper, and subsequent washing of the paper with a dilute solution of phosphoric acid, in the case of a peptide substrate, or by application of the reaction products to a gel electrophoresis system followed by autoradiographic detection in the case of proteins. Other methods well known in the art are available to conveniently measure the IKR-1 and/or IKR-2-mediated transfer of phosphate to substrate proteins, such as the scintillation proximity assay.

The specification is most thoroughly understood in light of the teachings of the references cited within the specification which are hereby incorporated by reference. The embodiments within the specification provide an illustration of embodiments of the invention and should not be construed to limit the scope of the invention. The skilled artisan readily recognizes that many other embodiments are encompassed by the invention.

What is claimed is:

1. An isolated nucleic acid molecule selected from the group consisting of:
   (a) a polynucleotide molecule having the sequence of SEQ ID NO:3;
   (b) a polynucleotide molecule encoding an amino acid sequence comprising the sequence of SEQ ID NO:4; and
   (c) a polynucleotide molecule, or its complement, that hybridizes to a denatured DNA molecule comprising the nucleic acid sequence of (a) in 50% formamide and 6×SSC at 42 degrees C., and washing in 0.2×SSC and 0.1% SDS at 68 degrees C., wherein the polynucleotide molecule encodes a polypeptide having kinase activity.

2. A recombinant vector that directs the expression of the nucleic acid of claim 1.

3. A host cell comprising the vector of claim 2.

4. A method for the production of a polypeptide encoded by a polynucleotide molecule of claim 1, comprising culturing a recombinant host cell in a suitable culture medium, said recombinant host cell comprising a control sequence operably linked to a polynucleotide encoding said polypeptide.

5. The method of claim 4, wherein the host cell is selected from the group consisting of bacterial cells, yeast cells, plant cells, and animal cells.

6. The method of claim 4 further comprising recovering the polypeptide from the cell or culture medium.

7. An isolated polynucleotide molecule that encodes a polypeptide having kinase activity and comprising amino acids 1–300 of SEQ ID NO:4.

8. An isolated polynucleotide molecule encoding a polypeptide having kinase activity, the polynucleotide molecule comprising a nucleotide sequence selected from the group consisting of:

(a) a nucleotide sequence encoding an amino acid sequence selected from the group consisting of amino acids 1 through 53 of SEQ ID NO:4, amino acids 1 through 300 of SEQ ID NO:4, amino acids 2 through 53 of SEQ ID NO:4, amino acids 143 through 234 of SEQ ID NO:4, amino acids 185 through 234 of SEQ ID NO:4, amino acids 185 through 309 of SEQ ID NO:4, amino acids 310 through 319 of SEQ ID NO:4, amino acids 310 through 414 of SEQ ID NO:4, amino acids 320 through 414 of SEQ ID NO:4, amino acids 320 through 439 of SEQ ID NO:4, amino acids 415 through 439 of SEQ ID NO:4, amino acids 415 through 486 of SEQ ID NO:4, amino acids 440 through 486 of SEQ ID NO:4, amino acids 440 through 598 of SEQ ID NO:4, amino acids 487 through 598 of SEQ ID NO:4, amino acids 487 through 620 of SEQ ID NO:4, amino acids 599 through 620 of SEQ ID NO:4, amino acids 599 through 623 of SEQ ID NO:4, amino acids 624 through 662 of SEQ ID NO:4, amino acids 624 through 673 of SEQ ID NO:4, amino acids 663 through 673 of SEQ ID NO:4, amino acids 663 through 686 of SEQ ID NO:4, amino acids 674 through 686 of SEQ ID NO:4, and amino acids 674 through 690 of SEQ ID NO:4;

(b) a nucleotide sequence of (a), wherein said nucleotide sequence is a fragment of SEQ ID NO:3;

(c) the nucleotide sequence of a polynucleotide molecule, or its complement, that hybridizes to a denatured DNA molecule comprising the nucleotide sequence of (b) in 50% formamide and 6×SSC at 42 degrees C., and washing in 0.2×SSC and 0.1% SDS at 68 degrees C., wherein the nucleotide sequence encodes a polypeptide having kinase activity; and (d) a nucleotide sequence that is at least 90% identical to the nucleotide sequence of (b), wherein the nucleotide sequence encodes a polypeptide having kinase activity.

9. The isolated polynucleotide molecule of claim 8, wherein the polynucleotide molecule comprises a nucleotide sequence selected from the group consisting of:

(a) a nucleotide sequence encoding an amino acid sequence selected from the group consisting of amino acids 1 through 53 of SEQ ID NO:4, amino acids 1 through 300 of SEQ ID NO:4, amino acids 2 through 53 of SEQ ID NO:4, amino acids 143 through 234 of SEQ ID NO:4, amino acids 185 through 234 of SEQ ID NO:4, amino acids 185 through 309 of SEQ ID NO:4;

(b) a nucleotide sequence of (a), wherein said nucleotide sequence is a fragment of SEQ ID NO:3;

(c) the nucleotide sequence of a polynucleotide molecule, or its complement, that hybridizes to a denatured DNA molecule comprising the nucleotide sequence of (b) in 50% formamide and 6×SSC at 42 degrees C., and washing in 0.2×SSC and 0.1% SDS at 68 degrees C., wherein the nucleotide sequence encodes a polypeptide having kinase activity; and (d) a nucleotide sequence that is at least 90% identical to the nucleotide sequence of (b), wherein the nucleotide sequence encodes a polypeptide having kinase activity.

10. The isolated polynucleotide molecule of claim 9, wherein the polynucleotide molecule comprises a nucleotide sequence encoding an amino acid sequence selected from the group consisting of: amino acids 1 through 53 of SEQ ID NO:4, amino acids 1 through 300 of SEQ ID NO:4, amino acids 2 through 53 of SEQ ID NO:4, amino acids 143 through 234 of SEQ ID NO:4, amino acids 185 through 234 of SEQ ID NO:4, and amino acids 185 through 309 of SEQ ID NO:4.

11. The isolated polynucleotide molecule of claim 8, wherein the polynucleotide molecule comprises a nucleotide sequence encoding amino acids 143 through 234 of SEQ ID NO:4.

12. The isolated polynucleotide molecule of claim 8, wherein the polynucleotide molecule comprises a nucleotide sequence encoding amino acids 185 through 234 of SEQ ID NO:4.

13. The isolated polynucleotide molecule of claim 8, wherein the polynucleotide molecule comprises a nucleotide sequence encoding amino acids 185 through 309 of SEQ ID NO:4.

14. A recombinant vector that directs the expression of a polynucleotide molecule of claim 7.

15. A host cell comprising the vector of claim 14.

16. A method for the production of a polypeptide encoded by a polynucleotide molecule of claim 7, comprising culturing a recombinant host cell in a suitable culture medium, said recombinant host cell comprising a control sequence operably linked to a polynucleotide encoding said polypeptide.

17. The method of claim 16, wherein the host cell is selected from the group consisting of bacterial cells, yeast cells, plant cells, and animal cells.

18. The method of claim 16 further comprising recovering the polypeptide from the cell or culture medium.

19. A recombinant vector that directs the expression of a polynucleotide molecule of claim 8.

20. A host cell comprising the vector of claim 17.

21. A method for the production of a polypeptide encoded by a polynucleotide molecule of claim 8, comprising culturing a recombinant host cell in a suitable culture medium, said recombinant host cell comprising a control sequence operably linked to a polynucleotide encoding said polypeptide.

22. The method of claim 21, wherein the host cell is selected from the group consisting of bacterial cells, yeast cells, plant cells, and animal cells.

23. The method of claim 21 further comprising recovering the polypeptide from the cell or culture medium.

* * * * *